United States Patent
Jung et al.

(10) Patent No.: US 10,360,678 B2
(45) Date of Patent: Jul. 23, 2019

(54) IMAGE PROCESSING APPARATUS, IMAGE PROCESSING METHOD AND RECORDING MEDIUM THEREOF

(71) Applicant: SAMSUNG ELECTRONICS CO., LTD., Suwon-si, Gyeonggi-do (KR)

(72) Inventors: Yun-sub Jung, Yongin-si (KR); Gye-hyun Kim, Seoul (KR); Jae-sung Lee, Seoul (KR); Yong-sup Park, Seoul (KR); Ji-hun Oh, Hwaseong-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 58 days.

(21) Appl. No.: 15/430,846

(22) Filed: Feb. 13, 2017

(65) Prior Publication Data

US 2017/0236275 A1 Aug. 17, 2017

(30) Foreign Application Priority Data

Feb. 15, 2016 (KR) .......................... 10-2016-0017479

(51) Int. Cl.
*G06T 7/62* (2017.01)
*A61B 5/107* (2006.01)
(Continued)

(52) U.S. Cl.
CPC .......... *G06T 7/0012* (2013.01); *A61B 5/0062* (2013.01); *A61B 5/0066* (2013.01);
(Continued)

(58) Field of Classification Search
CPC ......... G06T 7/0012; G06T 2207/30004; G06T 2207/10081; G06T 2207/10072;
(Continued)

(56) References Cited

U.S. PATENT DOCUMENTS 9,125,621 B2 * 9/2015 Nagatsuka ............... A61B 5/08
2002/0115923 A1 8/2002 Erbel
(Continued)

FOREIGN PATENT DOCUMENTS

| EP | 1 633 246 | 11/2008 |
|---|---|---|
| KR | 10-2010-0008810 | 1/2010 |
| WO | 03/022134 | 3/2003 |

OTHER PUBLICATIONS

Deshmukh et al., MR Assessment of Normal Fetal Lung Volumes: A Literature Review, Feb. 2010[retrieved Jun. 20, 2018], American Journal of Roentgenology, vol. 194, No. 2, pp. W212-W217. Retrieved from the Internet: https://www.ajronline.org/doi/abs/10.2214/AJR.09.2469.*

(Continued)

*Primary Examiner* — Andrew M Moyer
*Assistant Examiner* — Dennis Rosario
(74) *Attorney, Agent, or Firm* — Nixon & Vanderhye P.C.

(57) ABSTRACT

Disclosed are an image processing apparatus, an image processing method and a recording medium thereof, the image processing apparatus including: a storage configured to store standard information about at least one anatomical entity; and at least one processor configured to detect regions corresponding to a plurality of anatomical entities based on a medical image obtained by scanning an object including the plurality of anatomical entities, to estimate a volume of a first anatomical entity at a predetermined point in time based on object information measured from the detected regions of the anatomical entity and the standard information stored in the storage, and to provide information about condition of the first anatomical entity based on the estimated volume. Thus, it is possible to make a diagnosis more simply and accurately by determining condition infor- (Continued)

mation of an anatomical entity at a point in time for the diagnosis based on a randomly taken medical image.

20 Claims, 16 Drawing Sheets

(51) Int. Cl.
| | |
|---|---|
| *A61B 5/087* | (2006.01) |
| *G06T 7/00* | (2017.01) |
| *G06T 7/11* | (2017.01) |
| *A61B 5/055* | (2006.01) |
| *A61B 5/08* | (2006.01) |
| *A61B 5/00* | (2006.01) |
| *A61B 6/03* | (2006.01) |
| *A61B 6/00* | (2006.01) |
| *A61B 8/00* | (2006.01) |
| *A61B 8/08* | (2006.01) |
| *A61B 5/01* | (2006.01) |
| *A61B 5/0402* | (2006.01) |

(52) U.S. Cl.
CPC .............. *A61B 5/01* (2013.01); *A61B 5/0402* (2013.01); *A61B 5/055* (2013.01); *A61B 5/08* (2013.01); *A61B 5/087* (2013.01); *A61B 5/1073* (2013.01); *A61B 5/7278* (2013.01); *A61B 5/742* (2013.01); *A61B 6/032* (2013.01); *A61B 6/461* (2013.01); *A61B 6/50* (2013.01); *A61B 6/5217* (2013.01); *A61B 6/5288* (2013.01); *A61B 6/566* (2013.01); *A61B 8/0858* (2013.01); *A61B 8/461* (2013.01); *A61B 8/5223* (2013.01); *A61B 8/565* (2013.01); *G06T 7/11* (2017.01); *G06T 7/62* (2017.01); *A61B 8/08* (2013.01); *A61B 2576/02* (2013.01); *G06T 2207/10081* (2013.01); *G06T 2207/10088* (2013.01); *G06T 2207/10116* (2013.01); *G06T 2207/10132* (2013.01); *G06T 2207/30008* (2013.01); *G06T 2207/30061* (2013.01); *G06T 2207/30242* (2013.01); *G06T 2211/404* (2013.01)

(58) Field of Classification Search
CPC .................. G06T 7/62; G06T 2200/04; G06T 2207/10088; G06T 2207/10116; G06T 7/0014; G06T 2207/30061; G06T 2210/41; G06T 2207/10132; G06T 7/0016; G06T 2207/10076; G06T 7/60; A61B 6/037; A61B 5/1118; A61B 5/0205; A61B 5/087; A61B 5/055; A61B 5/1135; A61B 5/113; A61B 5/1128; A61B 5/091; A61B 5/103; A61B 5/107; A61B 5/1073
See application file for complete search history.

(56) References Cited

U.S. PATENT DOCUMENTS

| | | |
|---|---|---|
| 2003/0055331 A1 | 3/2003 | Kotmel et al. |
| 2010/0249580 A1 | 9/2010 | Goto et al. |
| 2015/0005659 A1 | 1/2015 | Masumoto |
| 2015/0351714 A1 | 12/2015 | De Backer |

OTHER PUBLICATIONS

Chu et al., Dynamic Magnetic Resonance Imaging in Assessing Lung Volumes, Chest Wall, and Diaphragm Motions in Adolescent Idiopathic Scoliosis Versus Normal Controls, Sep. 1, 2006[ret Jun. 20, 2018], Spine, vol. 31, Iss 19,p. 2243-2249. https://journals.lww.com/spinejournal/Fulltext/2006/09010/Dynamic_Magnetic_Resonance_Imaging_in_Assessing.15.aspx.*

Plathow et al., Evaluation of Chest Motion and Volumetry During the Breathing Cycle by Dynamic MRI in Healthy Subjects, Apr. 2004[retrieved Jun. 20, 2018], Investigative Radiology, vol. 39, Issue 4,pp. 202-209. Internet: https://journals.lww.com/investigativeradiology/Fulltext/2004/04000/Evaluation_of_Chest_Motion_and_Volumetry_During.2.aspx.*

Gierada et al., MR Analysis of Lung Volume and Thoracic Dimensions in Patients with Emphysema Before and After Lung Volume Reduction Surgery, Mar. 1998[ret Jun. 20, 2018], American Journal of Roentgenology, vol. 170, Issue 3,pp. 707-714. Internet: https://www.ajronline.org/doi/abs/10.2214/ajr.170.3.9490958.*

Search Report dated May 26, 2017 in counterpart International Patent Application No. PCT/KR2017/001573.

Kang et al., "Measurement of Lung Volumes by Spiral Ct: Comparison With Pulmonary Function Test", *Journal of the Korean Radiological Society*, 1996, vol. 35(5), pp. 709-714 and English Translation.

Lu et al., "Comparison of spirometry and abdominal height as four dimensional computed tomography metrics in lung", *Am. Assoc. Phys. Med.*, vol. 32(7), Jul. 2005, pp. 2351-2357.

Kim et al., "The effect of pulmonary function and chest length in the stroke patients after feedback breathing exercise among position changes", *Journal of Special Education & Rehabilitation Science*, 2010, vol. 49, No. 3, pp. 57-74.

Mackenzie et al., "Dynamic changes in the zone of apposition and diaphragm length during maximal respiratory efforts", *Thorax*, 1994; 49: pp. 634-638.

Park, et al., "The effect of the correlation between the contraction of the pelvic floor muscles and diaphragmatic motion during breathing", *Jour. of Phys. Ther. Sci.*, 2015, 27, pp. 2113-2115.

* cited by examiner

IMAGE PROCESSING APPARATUS, IMAGE PROCESSING METHOD AND RECORDING MEDIUM THEREOF

CROSS-REFERENCE TO RELATED APPLICATION

This application is based on and claims priority under 35 U.S.C. § 119 to Korean Patent Application No. 10-2016-0017479, filed on Feb. 15, 2016 in the Korean Intellectual Property Office, the disclosure of which is incorporated by reference herein in its entirety.

BACKGROUND

Field

The present disclosure relates generally to an image processing apparatus, an image processing method and a recording medium thereof, which offers information for diagnosing condition of a predetermined object based on information measured from a medical image.

Description of Related Art

A medical image shows a user an inner structure of an object such as structural details, internal organs, fluid flow, etc. of a photographed and processed body. Through the medical image, a doctor or the like user checks health condition of a patient and diagnoses a disease.

The medical image includes a magnetic resonance image (MRI), a computed tomography (CT) image, an X-ray image, and an ultrasound image, etc. The medical image represents an object in various ways in accordance with the kinds and photographing methods of photographing devices.

As a pulmonary function test, spirometry uses a pneumatometer (or a respirometer) to measure and calculate vital capacity (VC), inspiratory reserve volume (IRV), expiratory reserve volume (ERV), etc. and combines the results, thereby assessing a pulmonary function.

In general, the spirometry cannot measure residual volume (RV) and has shortcomings of low reproducibility. Therefore, the spirometry is hardly used in confirming a specific lung disease, and its range of use is limited to such an extent that the spirometry is mostly used in determining whether the pulmonary function is normal or abnormal.

Accordingly, there is a need of image processing, in which a medical image, e.g., a chest image is used in the pulmonary function test to thereby more accurately obtain diagnosis results of various pulmonary functions.

SUMMARY

According to an aspect of an example embodiment, an image processing apparatus is provided, including: a storage configured to store standard information about at least one anatomical entity; and at least one processor configured to detect regions corresponding to a plurality of anatomical entities based on a medical image obtained by scanning an object including the plurality of anatomical entities, to estimate a volume of a first anatomical entity at a predetermined point in time based on object information measured from the detected regions of the anatomical entity and the standard information stored in the storage, and to provide information about a condition of the first anatomical entity based on the estimated volume. Accordingly, it is possible to make a diagnosis more simply and accurately by determining condition information of an anatomical entity at a point in time of the diagnosis (e.g. at the maximum inspiration or the maximum expiration) based on a randomly taken medical image.

The object information may include a first measurement value of a second anatomical entity, and the standard information includes a first estimation value of a third anatomical entity corresponding to the first measurement value, the processor may determine the first estimation value corresponding to the first measurement value based on the standard information, and determine a volume of the first anatomical entity at the predetermined point in time from the first estimation value. Thus, it is possible to estimate information needed for making a diagnosis based on information about entities around an object to be examined, e.g., an anatomical entity.

The object information may further include a second measurement value of the first anatomical entity and a third measurement value of the third anatomical entity, and the processor may determine the volume of the first anatomical entity at the predetermined point in time based on the first estimation value, the second measurement value and the third measurement value. Thus, it is convenient to estimate information about an entity at a point in time needed for making a diagnosis, through an equation using a measurement value of a medical image and an estimated value based on the measurement value.

The processor may use an Equation $$L_M = \frac{D_{RC} * L_N}{D_{NC}}$$

to determine the volume of the first anatomical entity at the predetermined point in time, $L_M$ corresponding to the volume of the first anatomical entity, $D_{RC}$ corresponding to the first estimation value, $L_N$ corresponding to the second measurement value, and $D_{NC}$ corresponding to the third measurement value. Thus, it is possible to estimate required information through calculation using a simple equation.

The processor may count a pixel number in the medical image to determine at least one index for providing information about condition of the first anatomical entity at a scanning time for the medical image, and determine at least one index at the predetermined point in time based on the determined index at the scanning time and the estimated volume of the first anatomical entity at the predetermined point in time. Thus, an index for offering information about condition of an anatomical entity is determined and provided as required information.

The processor may convert the counted pixel number into a volume, and determine at least one index at the predetermined point in time based on the estimated volume of the first anatomical entity at the predetermined point in time, the second measurement value at the scanning time for the medical image and the at least one index converted into the volume. Thus, an index is determined based on a relationship between the number of pixels and the volume from the information at the image taking time and the estimated volume information, and provided as condition information.

The index may include at least one among total lung capacity (TLC), vital capacity (VC) and residual volume (RV) used in a pulmonary function test. Thus, it is advantageous to utilize even an RV, which is difficult to be obtained in the existing spirometry, for making a diagnosis with respect to a lung.

The first anatomical entity may include a lung, and the predetermined point in time includes time of maximum inspiration or expiration, and the processor may estimate a volume of the lung. Thus, a volume of a lung at the maximum inspiration or the maximum expiration needed for a diagnosis is estimated from a randomly taken lung image, and it is thus possible to make a correct diagnosis of a lung disease.

The second anatomical entity may include a diaphragm, and the third anatomical entity includes ribs, and the first measurement value may include a length of the diaphragm, the second measurement value includes a volume of the lung at the scanning time for the medical image, and the third measurement value may include a diameter of a rib cage. Thus, organs around an object to be examined, e.g., a lung are utilized to obtain information needed for making a lung diagnosis and it is possible to estimate a volume of a long at the maximum inspiration or the maximum expiration through various measurement values of surrounding organs.

The standard information may be sorted in based on at least one of age, sex, height, weight and race and stored in the storage. Thus, results are reliable since verified standard information is used to estimate an object to be examined.

According to an aspect of an example embodiment, an image processing method is provided, including: detecting regions corresponding to a plurality of anatomical entities based on a medical image obtained by scanning an object including the plurality of anatomical entities; estimating a volume of a first anatomical entity at a predetermined point in time based on object information measured from the detected regions of the anatomical entity and standard information about at least one anatomical entity; and providing information about a condition of the first anatomical entity based on the estimated volume. Accordingly, it is possible to make a diagnosis more simply and accurately by determining condition information of an anatomical entity at a point in time for the diagnosis (e.g. at the maximum inspiration or the maximum expiration) based on a randomly taken medical image.

The object information may include a first measurement value of a second anatomical entity, and the standard information may include a first estimation value of a third anatomical entity corresponding to the first measurement value, the estimating the volume of the first anatomical entity may include determining the first estimation value corresponding to the first measurement value based on the standard information, and determining a volume of the first anatomical entity at the predetermined point in time from the first estimation value. Thus, it is possible to estimate information needed for making a diagnosis based on information about entities around an object to be examined, e.g., an anatomical entity.

The object information further may include a second measurement value of the first anatomical entity and a third measurement value of the third anatomical entity, and the estimating the volume of the first anatomical entity may include determining a volume of the first anatomical entity at the predetermined point in time based on the first estimation value, the second measurement value and the third measurement value. Thus, it is convenient to estimate information about an entity at a point in time needed for making a diagnosis, through an equation using a measurement value of a medical image and an estimated value based on the measurement value.

The estimating the volume of the first anatomical entity may include using an Equation $$L_M = \frac{D_{RC} * L_N}{D_{NC}}$$

to determine a volume of the first anatomical entity at the predetermined point in time, $L_M$ corresponding to the volume of the first anatomical entity, $D_{RC}$ corresponding to the first estimation value, $L_N$ corresponding to the second measurement value, and $D_{NC}$ corresponding to the third measurement value. Thus, it is possible to estimate required information through calculation using a simple equation.

The image processing method may further include: counting a pixel number in the medical image to determine at least one index for providing information about condition of the first anatomical entity at a scanning time for the medical image; and determining at least one index at the predetermined point in time based on the determined index at the scanning time and the estimated volume of the first anatomical entity at the predetermined point in time, and the providing information about condition of the first anatomical entity may include providing information about the condition of the first anatomical entity based on the at least one determined index at the predetermined point in time. Thus, an index for offering information about condition of an anatomical entity is determined and provided as required information.

The image processing method may further include converting the counted pixel number into a volume, and the determining the at least one index at the predetermined point in time may include determining at least one index at the predetermined point in time based on the estimated volume of the first anatomical entity at the predetermined point in time, the second measurement value at the scanning time for the medical image and the at least one index converted into the volume. Thus, an index is determined based on a relationship between the number of pixels and the volume from the information at the image taking time and the estimated volume information, and provided as condition information.

The index may include at least one among total lung capacity (TLC), vital capacity (VC) and residual volume (RV) used in a pulmonary function test, the first anatomical entity may include a lung, and the predetermined point in time may include time of maximum inspiration or expiration, and the estimating the volume of the first anatomical entity may include estimating a volume of the lung at the maximum inspiration or the maximum expiration. Thus, it is advantageous to utilize even an RV, which is difficult to be obtained in the existing spirometry, for making a diagnosis with respect to a lung and a volume of a lung at the maximum inspiration or the maximum expiration needed for a diagnosis is estimated from a randomly taken lung image, and it is thus possible to make a correct diagnosis of a lung disease.

The second anatomical entity may include a diaphragm, and the third anatomical entity may include ribs, and the first measurement value may include a length of the diaphragm, the second measurement value may include a volume of the lung at the scanning time for the medical image, and the third measurement value may include a diameter of a rib cage. Thus, organs around an object to be examined, e.g., a lung are utilized to obtain information needed for making a lung diagnosis and it is possible to estimate a volume of a long at the maximum inspiration or the maximum expiration through various measurement values of surrounding organs.

The standard information may be sorted based on at least one of age, sex, height, weight and race and previously stored in the storage, and the providing information about condition of the first anatomical entity may include using a display to provide information about condition of the first anatomical entity. Thus, results are reliable since verified standard information is used to estimate an object to be examined, and an apparatus capable of making a diagnosis of various diseases based on displayed information is provided.

According to an aspect of an example embodiment, a recording medium is provided in which a program for performing an image processing method is recorded as a computer-readable program, the image processing method including: detecting regions corresponding to a plurality of anatomical entities based on a medical image obtained by scanning an object including the plurality of anatomical entities; estimating a volume of a first anatomical entity at a predetermined point in time based on object information measured from the detected regions of the anatomical entity and standard information about at least one anatomical entity; and providing information about a condition of the first anatomical entity based on the estimated volume. Accordingly, it is possible to make a diagnosis more simply and accurately by determining condition information of an anatomical entity at a point in time for the diagnosis (e.g. at the maximum inspiration or the maximum expiration) based on a randomly taken medical image.

BRIEF DESCRIPTION OF THE DRAWINGS

The above and/or other aspects, features and attendant advantages of the present disclosure will become apparent and more readily appreciated from the following detailed description, taken in conjunction with the accompanying drawings, in which like reference numerals refer to like elements, and wherein.

DETAILED DESCRIPTION

Figure 1:
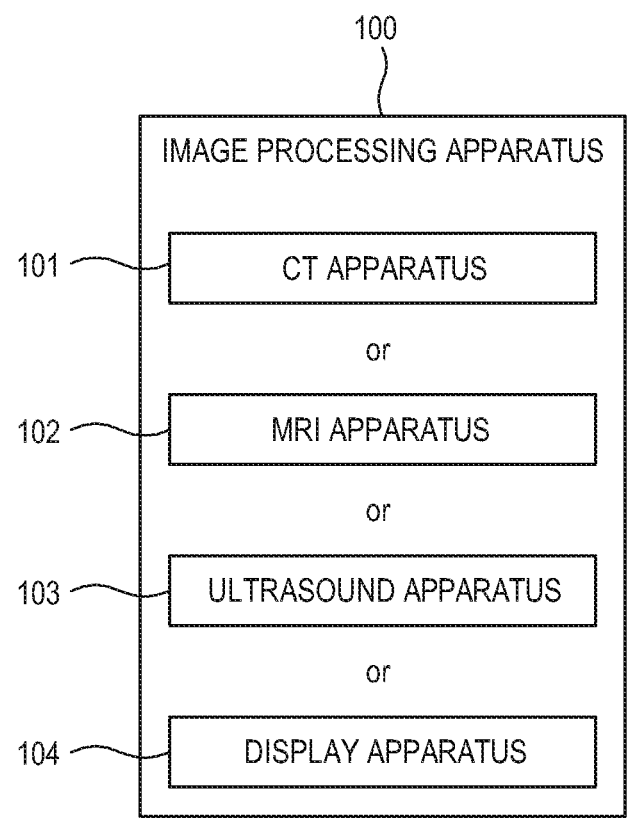
FIG. 1 is a diagram illustrating an example medical processing apparatus according to an example embodiment.

Below, various example embodiments will be described with reference to accompanying drawings to such an extent as to be easily understood by a person having an ordinary knowledge in the art. The present disclosure is not limited to the various example embodiments set forth herein.

Terms to be used in the following descriptions will be selected as general terms currently used as widely as possible taking functions of elements into account, but may be varied depending on intent of those skilled in the art, precedents, the advent of new technology, etc. For example, there may be a term that is arbitrarily selected. In this case, the meaning of the term will be explained in detail through the relevant detailed descriptions. Therefore, the terms set forth herein have to be read in light of its meaning and content throughout the following descriptions rather than by the term alone.

In the following descriptions, terms such as "include" or "have" refer to presence of features, numbers, steps, operations, elements or combination thereof, and do not exclude presence or addition of one or more other features, numbers, steps, operations, elements or combination thereof.

A "portion" set forth herein may refer, for example, to software or hardware such as, for example, and without limitation, processing circuitry, a dedicated processor, a CPU, FPGA or ASIC, or the like and performs certain roles. However, the meaning of the "portion" is not limited to software or hardware. The "portion" may be configured to be present in a storage medium for addressing or may be configured to reproduce one or more processors. For example, the "portion" includes software elements, object-oriented software elements, class elements, task elements and the like elements, and processes, functions, attributes, procedures, subroutines, segments of a program code, drivers, firmware, a microcode, a circuit, data, a database, data structures, tables, arrays and variables. The function provided in the elements and the "portions" may be carried out by combining fewer elements and "portions" or subdividing additional elements and "portions".

In this disclosure, an "image" may refer, for example, to multi-dimensional data with discrete image elements (e.g. pixels in a 2D image and voxels in a 3D image). For example, an image may include a medical image of an object taken by X-ray, CT, MRI, ultrasound and other medical image systems.

Further, in this disclosure, an "object" may include, for example, a human or an animal, or a part of the human or animal. For example, the object may include a liver, a heart, a uterus, a brain, a breast, an abdomen or the like organs; muscles or blood vessels. Further, the "object" may include a phantom. The phantom refers, for example, to a substance that has a volume very approximate to an effective atomic number and density of an organism, and may include a spherical phantom similar to a body.

Further, in this disclosure, a "user" may be a medical expert such as a doctor, a nurse, a medical laboratory technologist, a medical image expert, etc.; an engineer to fix a medical apparatus; or a patient, but is not limited thereto.

Further, in this disclosure, "information" may refer, for example, to anatomical information or functional information. In the following example embodiments, the functional information will be derived from the anatomical information.

Further, in this disclosure, a "lung volume" may refer to a real size of a lung (e.g., an anatomical volume) or a total amount of air contained in a lung (e.g., a functional volume), and will be thus properly understood as taking the present disclosure into account.

For clarity, elements not directly related to the elements of the example embodiment may be omitted, and like numerals refer to like elements throughout.

FIG. 1 is a diagram illustrating an example image processing apparatus 100 according to an example embodiment.

According to an example embodiment, the image processing apparatus 100 may be an apparatus that obtains a medical image and displays the obtained medical image on a screen. For example, as illustrated in FIG. 1, the image processing apparatus 100 may include a computed tomography (CT) apparatus 101, an X-ray apparatus (not shown), a magnetic resonance image (MRI) apparatus 102, an angiography apparatus (not shown), an ultrasound apparatus 103, etc. but not limited thereto.

The CT apparatus 101 may provide a cross-sectional image of an object (e.g., tomogram), and thus has advantages of representing an inner structure (e.g. a kidney, a lung and the like organs, or a diaphragm and the like muscle) of the object without overlapping as opposed to a general X-ray apparatus. The CT apparatus 101 may obtain a plurality of pieces of image data with a thickness not more than 2 mm for several tens to several hundreds of times per second and then may process the plurality of pieces of image data, thereby offering the relatively accurate cross-sectional images of the object.

The X-ray apparatus may refer, for example, to an apparatus that emits an X-ray to a human body and makes an image based on an inner structure of the human body. The angiography apparatus may refer, for example, to an apparatus that makes a blood vessel (an artery and a vein) of a person to be examined, in which a contrast medium is injected through a thin tube of about 2 mm, called a catheter, be seen through an X-ray.

The MRI apparatus 102 may refer, for example, to an apparatus that obtains a cross-sectional image of an object by representing strength of a magnetic resonance (MR) signal by a contrast with respect to a radio frequency (RF) signal generated in a magnetic field having a specific strength.

The ultrasound apparatus 103 may refer, for example, to an apparatus that emits an ultrasound signal from a body surface of an object toward a predetermined portion inside a body and obtains an image of a blood stream or plane-section of a soft tissue based on information about an ultrasound signal reflected from an organ inside the body (hereinafter, referred to as an ultrasound echo signal).

The image processing apparatus 100 according to an example embodiment may include a display apparatus 104 for processing a medical image to be displayable. The display apparatus 104 includes a desktop computer, a smart television (TV) or various apparatuses capable of processing an image, which may be achieved by not only a stationary terminal but also a mobile terminal, or the like, but is not limited thereto. As an example of the display apparatus 104 of the mobile terminal, there are a smart phone; a tablet computer or the like a smart pad; a laptop computer; a personal digital assistant (PDA) a personal portable information terminal, or the like, but is not limited thereto.

According to an example embodiment, the display apparatus 104 may include a predetermined application installed as a platform capable of processing or analyzing a medical image.

According to an example embodiment, when the application is executed, an input region for displaying various buttons as a user interface (hereinafter, may be referred to as a graphic user interface (GUI)) for a user's selection and a display region for displaying a medical image may be displayed on a screen. A user may use the UI on the input region of the application to open, e.g., load a medical image obtained by the medical apparatus such as the CT apparatus 101 or the like, and be offered the loaded medical image through the display region of the application. The displayed medical image includes a medical image processed for diagnosis.

According to an example embodiment, information about condition of a predetermined anatomical entity (for example, a lung) included in the medical image is provided through the display region of the application.

According to an example embodiment, the image processing apparatus 100 may exchange medical image data with a hospital server or other medical apparatuses in a hospital connected through, for example, a picture archiving and communication system (PACS). Further, the image processing apparatus 100 may perform data communication with the server or the like in accordance with standards of digital imaging and communications in medicine (DICOM).

According to an example embodiment, the image processing apparatus 100 may include a touch screen. The touch screen may be configured to detect a touch input position, a touched area and a touch input pressure. Further, the touch screen may be also configured to detect not only real-touch but proximity-touch.

In this disclosure, the real-touch refers to that a screen is actually touched with a user's body (e.g. a finger) or a touch pen as a touch tool (e.g. a pointing device, a stylus, a haptic pen, an electronic pen, etc.), and the proximity-touch refers to that user's body or a touch tool does not really touch but moves near a screen within a predetermined distance (e.g. hovers within a detectable distance of 30 mm or less).

The touch screen may be for example achieved by a resistive type, a capacitive type, an infrared type or an acoustic-wave type, or the like, but is not limited thereto.

According to an example embodiment, the image processing apparatus 100 may sense a gesture input as a user's touch input to a medical image through the touch screen.

In this disclosure, a user's touch input may include, for example, and without limitation, a tap, a click stronger than the tap, touch and hold, a double-tap, a double-click, drag of moving a touched state as much as a predetermined distance, drag and drop, a slide, flicking, panning, a swipe, a pinch, etc. Here, the drag, the slide, the flicking, the swipe or the like input may be divided into press of a finger (or a touch pen) against the touch screen, move as much as a predetermined distance, and release from the touch screen, and may include both straight move and curved move. The foregoing various touch inputs are included in the gesture input.

According to an example embodiment, the image processing apparatus 100 provides some or all of the buttons for controlling the medical image in the form of a GUI.

Figure 2:
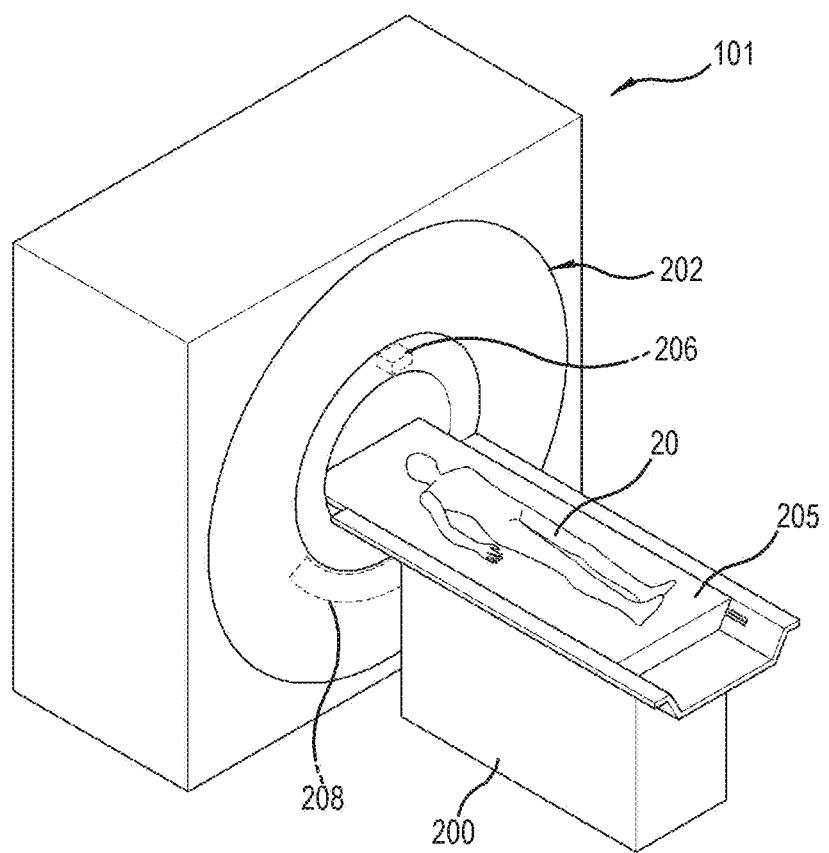
FIG. 2 is a diagram illustrating an example computed tomography (CT) apparatus as an image processing apparatus according to an example embodiment.
Figure 3:
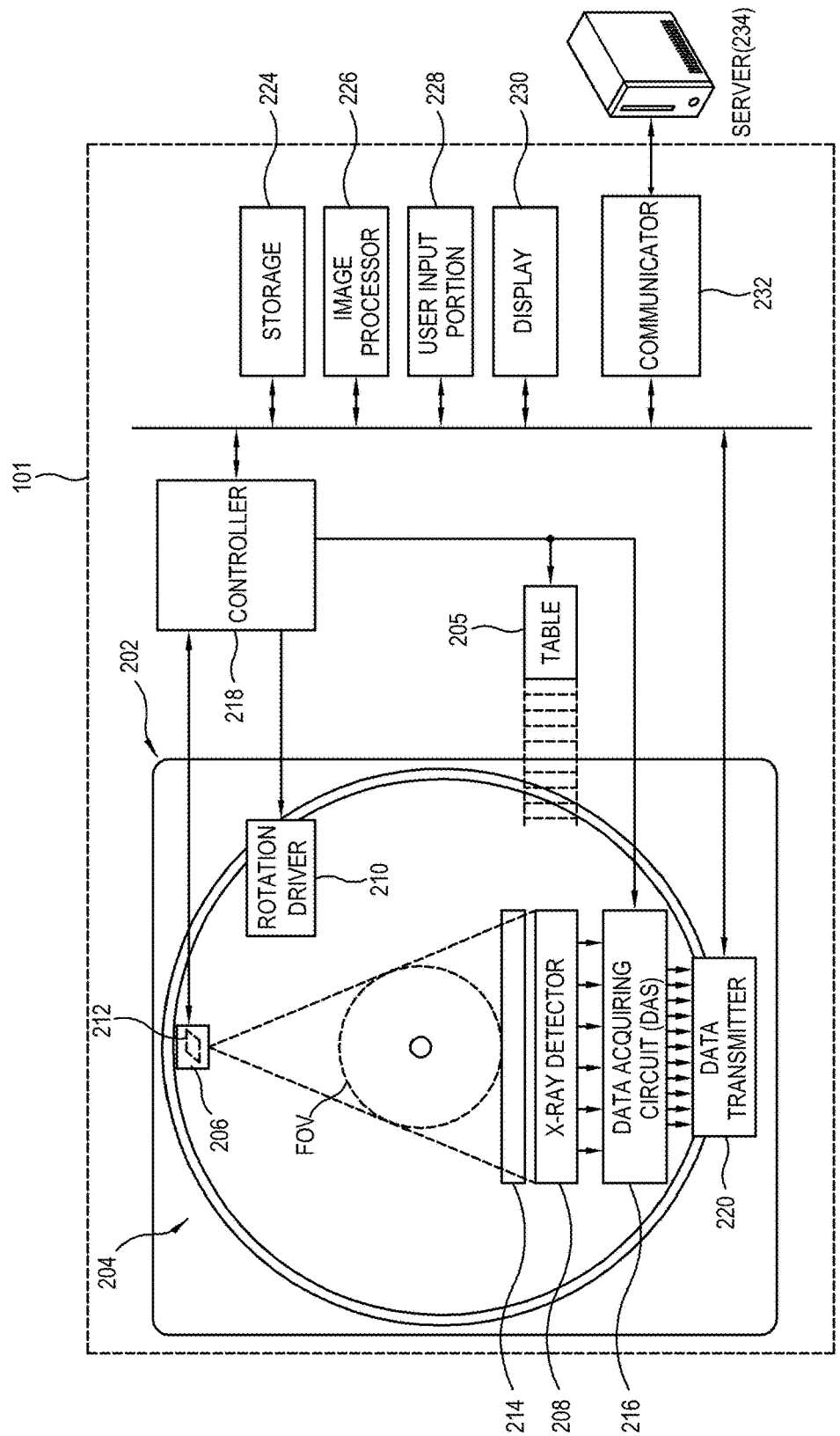
FIG. 3 is a diagram illustrating the CT apparatus of FIG. 2.

FIG. 2 is a diagram illustrating an example computed tomography (CT) apparatus 101 as an image processing apparatus 100 according to an example embodiment, and FIG. 3 schematically illustrates the CT apparatus 101 of FIG. 2.

As illustrated in FIG. 2, the CT apparatus 101 may include a gantry 202, a table 205, an X-ray generator 206 and an X-ray detector 208.

The CT apparatus 101 or the like tomograph provides a cross-sectional image of an object, and thus has advantages of representing an inner structure (e.g. a kidney, a lung and the like organs, or a diaphragm and the like muscle) of the object without overlapping as opposed to a general X-ray apparatus.

The tomograph includes a CT apparatus, an optical coherence tomography (OCT) apparatus, or a positron emission tomography (PET)-CT apparatus and the like tomographs.

In this example embodiment, the cross-sectional image is an image obtained by doing a tomography scan with regard to an object in the tomograph, which may include an image based on data projected after emitting an X-ray or the like beam to the object. For example, the CT image may refer to a synthesized image of a plurality of X-ray images obtained by scanning an object while rotating at least one axis of the object.

Below, the CT apparatus 101 illustated in FIGS. 2 and 3 will be described as an example of a tomograph 200.

The CT apparatus 101 may obtain a plurality of pieces of image data with a thickness not more than 2 mm for several tens to several hundreds of times per second and then may process the plurality of pieces of image data, thereby offering relatively accurate cross-sectional images of the object. Conventionally, there is a problem that only a cross-section of an object is represented. However, this problem has been overcome by various image reconstruction methods. As a 3D image reconstruction method, there are the following example techniques.

Shade surface display (SSD): an early 3D image technique for displaying only voxels having a predetermined HU value.

Maximum intensity projection (MIP)/minimum intensity projection (MinIP): a 3D technique for displaying only voxels having the highest or lowest HU value among voxels which constitute an image.

Volume rendering (VR): a technique for adjusting color and transmittance of voxels, which constitute an image, in accordance with regions of interest.

Virtual endoscopy: a technique for endoscopy in a 3D image reconstructed by the VR or SSD technique.

Multi planar reformation (MPR): an imaging technique for reconstructing another cross-sectional image freely as desired by a user.

Editing: various techniques for arranging surrounding voxels so that regions of interest can be more easily observed in the VR.

VOI(voxel of interest): a technique for representing only selected regions by the VR.

The CT apparatus 101 according to an example embodiment will be described with reference to FIG. 2 and FIG. 3. According to an example embodiment, the CT apparatus 101 may include various elements as illustrated in FIG. 3.

The gantry 202 may include the X-ray generator 206 and the X-ray detector 208.

An object 20 may be placed on the table 205.

The table 205 may move in a predetermined direction (e.g. in at least one direction among up, down, left and right directions) during a CT scan. Further, the table 205 may be tilted or rotated at a predetermined angle toward a predetermined direction.

Further, the gantry 202 may be also tilted at a predetermined angle toward a predetermined direction.

As illustrated in FIG. 3, the CT apparatus 101 according to an example embodiment may include the gantry 202, the table 205, a controller 218, a storage 224, an image processor 226, a user input portion (e.g., including input circuitry) 228, a display 230 and a communicator (e.g., including communication circuitry) 232.

As described above, the object 20 may be placed on the table 205. According to an example embodiment the table 205 is movable in a predetermined direction (e.g. in at least one direction among up, down, left and right directions) under control of the controller 218.

According to an example embodiment the gantry 202 may include a rotary frame 204, the X-ray generator 206, the X-ray detector 208, a rotation driver 210, a data acquiring circuit 216, and a data transmitter 220.

According to an example embodiment the gantry 202 includes the rotary frame 204 shaped like a ring rotatable with respect to a predetermined rotation axis (RA). Further, the rotary frame 204 may be shaped like a disc.

The rotary frame 204 may include the X-ray generator 206 and the X-ray detector 208 arranged to face each other and to have a predetermined field of view (FOV). Further, the rotary frame 204 may include an anti-scatter grid 214. The anti-scatter grid 214 may be interposed in between the X-ray generator 206 and the X-ray detector 208.

In the CT apparatus 101, an X-ray radiation to be detected by a detector (or a photosensitive film) includes not only an attenuated primary radiation forming an effective image but also a scattered radiation deteriorating quality of an image. To transmit most of the primary radiation but attenuate the scattered radiation, the anti-scatter grid is interposed in between a patient and the detector (or the photosensitive film).

For example, the anti-scatter grid may be formed by alternately layering strips of lead foil and an interspace material such as a solid polymer material, a solid polymer or a fiber composite material. However, the anti-scatter grid is not necessarily limited to this structure.

The rotary frame 204 receives a driving signal from the rotation driver 210, and rotates the X-ray generator 206 and the X-ray detector 208 at predetermined speed. The rotary frame 204 may receive the driving signal and power from the rotation driver 210 through contact with a slip ring (not shown). Further, the rotary frame 204 may receive the driving signal and the power from the rotation driver 210 through wireless communication.

The X-ray generator 206 may generate and emit an X-ray by receiving voltage and current from a high-voltage generator (not shown) of a power distribution unit (PDU) through the slip ring (not shown). When the high-voltage generator applies a predetermined voltage (hereinafter, referred to as a 'tube voltage'), the X-ray generator 206 may generate X-rays having a plurality of energy spectrums corresponding to such a predetermined tube voltage.

The X-rays generated by the X-ray generator 206 are emitted to have a predetermined pattern through a collimator 212.

The X-ray detector 208 may be arranged to face toward the X-ray generator 206. The X-ray detector 208 may include a plurality of X-ray detecting devices. One X-ray detecting device may form a single channel, but not limited thereto.

The X-ray detector 208 detects the X-ray generated by the X-ray generator 206 and passed through the object 20, and generates an electric signal corresponding to the intensity of the detected X-ray.

The X-ray detector 208 may include an indirect-type detector that detects light after converting the radiation into the light, and a direct-type detector that detects the radiation as an electric charge. The indirect-type X-ray detector may employ a scintillator. Further, the direct-type X-ray detector may employ a photon counting detector. The data acquiring circuit (or a data-acquisition system (DAS) 216 may connect with the X-ray detector 208. The electric signal generated by the X-ray detector 208 may be collected in the DAS 216. The electric signal generated by the X-ray detector 208 may be collected in the DAS 216 by a wire or wirelessly. Further, the electric signal generated by the X-ray detector 208 may be sent to an analog/digital converter (not shown) through an amplifier (not shown).

In accordance with the thickness of slice or the number of slices, only some pieces of data collected from the X-ray detector 208 may be sent to the image processor 226 or may be selected by the image processor 226.

Such a digital signal may be transmitted to, e.g., provided to the image processor 226 through the data transmitter 220 by a wire or wirelessly.

According to an example embodiment the controller 218 of the CT apparatus 101 may control operations of respective modules in the CT apparatus 101. For example, the controller 218 may control the operations of the table 205, the rotation driver 210, the collimator 212, the DAS 216, the storage 224, the image processor 226, the user input portion 228, the display 230, the communicator 232, etc.

The image processor 226 receives data (e.g. pure data before processing) acquired in the DAS 216 through the data transmitter 220, and applies pre-processing to the received data.

The pre-processing may for example include a process of balancing sensitivity between channels, a process of compensating for sudden decrease in signal strength or a signal loss due to metal or the like material of absorbing an X-ray, etc.

The data output from the image processor 226 may be called raw data or projection data. The projection data may be stored in the storage 224 together with scanning conditions at acquiring the data (e.g. a tube voltage, a scanning angle, etc.)

The projection data may be a set of data corresponding to intensity of an X-ray passed through an object. For convenience of description, a set of projection data simultaneously acquired at the same scanning angle with respect to all channels will be called a projection data set.

The storage 224 may include at least one-type storage medium among a flash memory type, a hard disk type, a multimedia card micro type, a card type memory (e.g. an SD memory, an XD memory, etc.), a random access memory (RAM), a static random access memory (SRAM), a read only memory (ROM), an electrically erasable programmable read-only memory (EEPROM), a programmable read-only memory (PROM), a magnetic memory, a magnetic disk, an optical disc, or the like, but is not limited thereto.

Further, the image processor 226 may restructure a cross-sectional image of an image based on a set of acquired projection data. Such a cross-sectional image may include a 3D image. In other words, the image processor 226 may use a cone beam reconstruction or the like method to generate a 3D image of an object based on the set of acquired projection data.

The user input portion 228 may include various input circuitry configured to receive an external input with regard to X-ray tomography conditions, image processing conditions, etc. For example, the X-ray tomography conditions may include a plurality of tube voltages, energy levels set for a plurality of X-rays, selection of scanning protocols, selection of image-reconstruction methods, setting of FOV regions, the number of slices, a slice thickness, settings of image post-processing parameters, etc. Further, the image processing conditions may include a resolution of an image, an attenuation coefficient set for image, a combination ratio set for an image, etc.

The user input portion 228 may include a device or the like for receiving a predetermined input from the outside. For example, the user input portion 228 may include various input circuitry, such as, for example, and without limitation, a microphone, a keyboard, a mouse, a joystick, a touch pad, a touch pen, a voice/gesture recognition device, etc.

The display 230 displays an X-ray scan image reconstructed by the image processor 226.

The data, power and the like may be transmitted and received between the foregoing elements by at least one of wired, wireless and optical communications.

The communicator 232 may include various circuitry configured to perform communication with an external device, an external medical apparatus, or the like, through a server 234 or the like.

Figure 4:
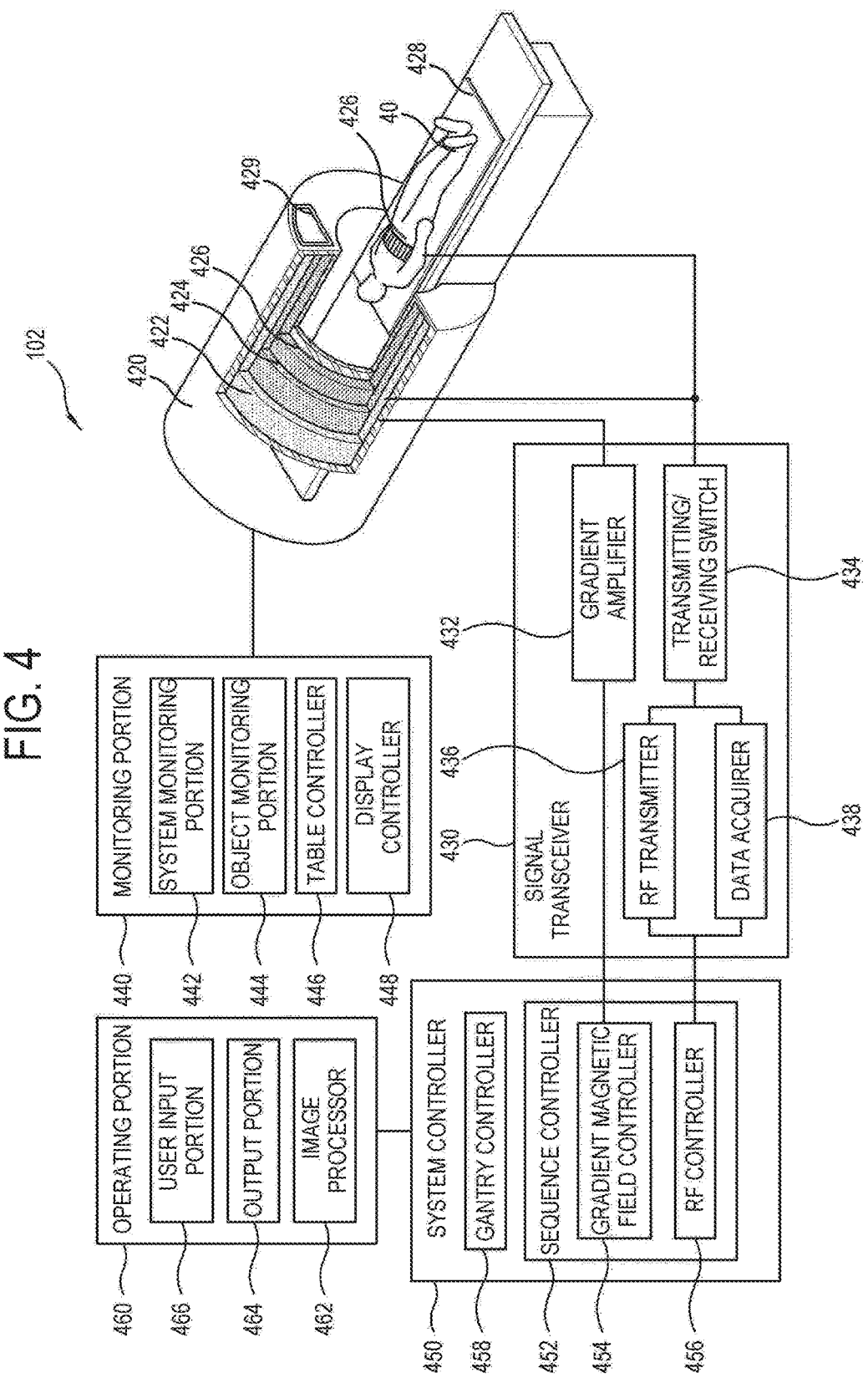
FIG. 4 is a diagram illustrates an example magnetic resonance image (MRI) apparatus as an image processing apparatus according to an example embodiment.

FIG. 4 is a diagram illustrating an example magnetic resonance image (MRI) apparatus 102 as an image processing apparatus 100 according to an example embodiment.

In this example embodiment, the magnetic resonance image (MRI) may refer, for example, to an image of an object obtained based on a principle of nuclear magnetic resonance.

The MRI apparatus 102 is an apparatus for obtaining an image of a tomography section of an object by representing strength of a magnetic resonance (MR) signal contrast into contrast with regard to a radio frequency (RF) signal generated in a magnetic field of specific strength. For example, if an object lies within a strong magnetic field and an RF signal for causing a resonance with only a specific atomic nucleus (e.g. a hydrogen atomic nucleus) is instantaneously emitted to the object and then suspended, the specific atomic nucleus generates an MR signal. The MRI apparatus 102 receives this MR signal and thus acquire an MR image. The MR signal refers to an RF signal radiated from the object. The strength of the MR signal may be determined by concentration of a predetermined atom (e.g. hydrogen) contained in the object, a relaxation time T1, a relaxation time T2, a blood stream, etc.

The MRI apparatus 102 has different features from other imaging apparatuses. As opposed to the CT apparatus and the like imaging apparatuses in which image acquisition depends on a direction of a detecting hardware image, the MRI apparatus 102 can acquire a 2D image or 3D volume image oriented toward a predetermined point. Further, the MRI apparatus 102 does not make an object or a person to be examined be exposed to a radiation unlike the CT, X-ray, PET and SPECT apparatus, and is used in acquiring a neurological image, a blood vessel intravascular image, a musculoskeletal image, an oncologic image or the like, in which it is important to clearly show an abnormal tissue, since it is capable of acquiring an image showing a high contrast in soft tissue.

As illustrated in FIG. 4, the MRI apparatus 102 in this example embodiment may include a gantry 420, a signal transceiver 430, a monitoring portion 440, a system controller 450 and an operating portion 460.

The gantry 420 prevents electromagnetic waves generated by a main magnet 422, a gradient coil 424, an RF coil 426, etc. from radiating to the outside. In a bore of the gantry 420, a static magnetic field and a gradient magnetic field are formed, and an RF signal is emitted to an object 40.

The main magnet 422, the gradient coil 424 and the RF coil 426 may be arranged along a predetermined direction of the gantry 420. The predetermined direction may include a coaxial cylindrical direction, etc. The object 40 may lie on a table 428 that can be inserted inside a cylinder along a horizontal axis of the cylinder.

The main magnet 422 generates a static magnetic field for arranging magnetic dipole moment of atomic nuclei included in the object 40 in a certain direction. As the strength and uniformity of the magnetic field generated by the main magnet are increased, an MR image of the object 40 is more accurate and correct.

The gradient coil 424 includes X, Y and Z coils for generating the gradient magnetic field in X, Y and Z-axial directions orthogonal to one another. The gradient coil 424 induces resonant frequencies different according to parts of the object 40 and thus provided position information about each part of the object 40.

The RF coil 426 emits an RF signal to a patient and receives an MR signal radiated from the patient. Specifically, the RF coil 426 transmits an RF signal, which has the same frequency as a frequency of precession of an atomic nucleus, to a patient, stops transmitting the RF signal, and receives an MR signal radiated from the patient.

For example, the RF coil 426 may generate an electromagnetic signal, e.g. an RF signal having a radio frequency corresponding to the kind of atomic nucleus in order for the atomic nucleus to have transition from a low energy state to a high energy state, and applies this RF signal to the object 40. If the electromagnetic signal generated by the RF coil 426 is applied to a certain atomic nucleus, this atomic nucleus may have transition from the low energy state to the high energy state. Then, if the electromagnetic waves generated by the RF coil 426 are removed, the atomic nucleus emits electromagnetic waves having the Larmor frequency by transition from the high energy state to the low energy state. In other words, if the electromagnetic signal applied to the atomic nucleus is cut off, the transition from a high energy level to a low energy level causes the atomic nucleus to generate the electromagnetic waves having the Larmor frequency. The RF coil 426 may receive an electromagnetic signal radiated from the atomic nuclei of the object 40.

The RF coil 426 may be achieved by a single RF transmitting/receiving coil that has a function of generating electromagnetic waves having a radio frequency corresponding to the kind of atomic nucleus, and a function of receiving electromagnetic waves radiated from the atomic nucleus. Alternatively, there may be separately provided a transmitting RF coil for generating electromagnetic waves having a radio frequency corresponding to the kind of atomic nucleus, and a receiving RF coil for receiving electromagnetic waves radiated from the atomic nucleus.

Further, the RF coil 426 may be integrated into the gantry 420, or detachably provided in the gantry 420. The detachable RF coil 426 may include a head RF coil, a chest RF coil, a leg RF coil, a neck RF coil, a shoulder RF coil, a wrist RF coil, an ankle RF coil, or the like RF coil corresponding to a part of the object.

Further, the RF coil 426 may communicate with an external device by a wire and/or wirelessly, and may perform dual-tune communication according to a communication frequency band.

Further, the RF coil 426 may include a birdcage coil, a surface coil and a transverse electromagnetic (TEM) coil in accordance with structures of the coil.

Further, the RF coil 426 may include a transmitting coil, a receiving coil and a transmitting/receiving coil in accordance with methods of transmitting and receiving an RF signal.

Further, the RF coil 426 may include RF coils for various channels such as 16 channels, 32 channels, 72 channels, 144 channels, etc.

Below, it will be described that the RF coil 426 is an RF multi coil including N coils corresponding to multi channels such as the first to the Nth channels. Here, the RF multi coil may be also called a multi-channel RF coil.

The gantry 420 may further include a display 429 placed outside the gantry 420 and a display (not shown) placed inside the gantry 420. Through the displays placed inside and/or outside the gantry 420, a user or an object can be offered a predetermined piece of information.

The signal transceiver 430 may control the gradient magnetic field formed inside, e.g., in the bore of the gantry 420 in accordance with a predetermined MR sequence, and controls transmission of an RF signal and an MR signal.

The signal transceiver 430 may include a gradient amplifier 432, a transmitting/receiving switch 434, an RF transmitter 436 and an RF data acquirer 438.

The gradient amplifier 432 may send the gradient coil 424 a pulse signal for driving the gradient coil 424 included in the gantry 420 and generating a gradient magnetic field under control of a gradient magnetic field controller 454. By controlling the pulse signal transmitted from the gradient amplifier 432 to the gradient coil 424, it is possible to combine the gradient magnetic fields in the X, Y and Z-axial directions.

The RF transmitter 436 and the RF data acquirer 438 may drive the RF coil 426. The RF transmitter 436 transmits an RF pulse having the Larmor frequency to the RF coil 426, and the RF data acquirer 438 receives the MR signal received in the RF coil 426.

The transmitting/receiving switch 434 may control the direction of transmitting/receiving the RF signal and the MR signal. For example, the transmitting/receiving switch 434 makes the RF coil 426 transmit the RF signal to the object 40 during a transmitting mode, and makes the RF coil 426 receive the MR signal from the object 40 during a receiving mode. The transmitting/receiving switch 434 may be controlled by a control signal from the RF controller 456.

The monitoring portion 440 may monitor or control the gantry 420 or devices mounted to the gantry 420. The monitoring portion 440 may include a system monitoring portion 442, an object monitoring portion 444, a table controller 446 and a display controller 448.

The system monitoring portion 442 may monitor and control a state of a static magnetic field, a state of a gradient magnetic field, a state of an RF signal, a state of the RF coil, a state of the table, a state of a device for measuring body information of an object, a state of power supply, a state of a heat exchanger, a state of a compressor, etc.

The object monitoring portion 444 monitors condition of the object 40. For example, the object monitoring portion 444 may include a camera for observing a motion or position of the object 40, a spirometer for measuring respiration of the object 40, an electrocardiography measurer for measuring an electrocardiogram of the object 40, or a clinical thermometer for measuring a body temperature of the object 40.

The table controller 446 controls movement of the table 428 on which the object 40 lies. The table controller 446 may control the table 428 to move under sequence control of a sequence controller 452. For example, during a moving imaging scan for an object, the table controller 446 may continuously or intermittently move the table 428 under the sequence control of the sequence controller 452, and thus scan the object by a field of view (FOV) larger than the FOV of the gantry.

The display controller 448 controls the display 429 placed inside and/or outside the gantry 420. For example, the display controller 448 may control the display 429 placed outside and/or inside the gantry 420 to be turned on/off or display an image. Further, if a loudspeaker is placed inside or outside the gantry 420, the display controller 448 may control the loudspeaker to be turned on/off or make a sound.

The system controller 450 may include the sequence controller 452 for controlling a sequence of signals generated inside the gantry 420, and a gantry controller 458 for controlling the gantry 420 and devices mounted to the gantry 420.

The sequence controller 452 may include a gradient magnetic field controller 454 for controlling the gradient amplifier 432, and an RF controller 456 for controlling the RF transmitter 436, the RF data acquirer 438 and the transmitting/receiving switch 434. The sequence controller 452 may control the gradient amplifier 432, the RF transmitter 436, the RF data acquirer 438 and the transmitting/receiving switch 434 in accordance with a pulse sequence received from the operating portion 460.

Here, a pulse sequence refers to continuity of a signal repetitively applied in the MRI apparatus 102. The pulse sequence may include a time parameter of an RF pulse, for example, such as a repetition time (TR), time to echo (TE), etc.

In this example embodiment, the pulse sequence includes all the information needed for controlling the gradient amplifier 432, the RF transmitter 436, the RF data acquirer 438 and the transmitting/receiving switch 434, for example, such as strength of a pulse signal applied to the gradient coil 424, applying time, apply timing, and the like information.

The operating portion 460 may control operations of the whole MRI apparatus 102 while giving the pulse sequence information to the system controller 450.

The operating portion 460 may include an image processor 462 for processing an MR signal received from the RF data acquirer 438, an output portion 464 and a user input portion 466.

The image processor 462 processes the MR signal received from the RF data acquirer 438, and generates MR image data about the object 40.

The image processor 462 processes the MR signal received in the RF data acquirer 438 to undergo amplification, frequency conversion, phase detection, low frequency amplification, filtering and the like various signal processes.

The image processor 462 may for example assign digital data to a k space of a memory and apply 2D or 3D Fourier transform to this data, thereby restructuring image data.

Further, the image processor 462 may synthesize image data or perform differential operation as necessary. The synthesis may include addition to a pixel, an MIP process, etc. Further, the image processor 462 may process not only reconstruction image data but also synthesized or differential-operated image data to be stored in a memory (not shown) or an external server.

Further, various signal processes applied by the image processor 462 to the MR signal may be performed in parallel. For example, the plurality of MR signals received in the multi-channel RF coil is processed in parallel to thereby reconstruct the plurality of MR signals into image data.

The output portion 464 may output image data generated or restructured by the image processor 462 to a user. Further, the output portion 464 may output a user interface (UI), user information, object information and the like needed for a user to control the MRI system.

The output portion 464 may include various circuitry, such as, for example, and without limitation, a loudspeaker, a printer, a display, etc. There are no limits to a type of display. For example, the display may be achieved by various types such as liquid crystal, plasma, a light-emitting diode, an organic light-emitting diode, a surface-conduction electron-emitter, a carbon nano-tube, nano-crystal, etc. Further, the display may be achieved to display a 3D image. As necessary, the display may be achieved by a transparent display.

In this example embodiment, the output portion 464 may include various output devices that may be apparent to those skilled in the art.

A user uses the user input portion 466 to input object information, parameter information, scan conditions, pulse sequence, information about synthesis or differential operation for an image, etc. The user input portion 466 may include various input circuitry, such as, for example, and without limitation, a keyboard, a mouse, a track ball, a voice recognizer, a gesture recognizer, a touch pad, and the like various input devices that may be apparent to those skilled in the art.

FIG. 4 illustrates the signal transceiver 430, the monitoring portion 440, the system controller 450 and the operating portion 460 as modules separated from one another, but not limited thereto. It will be readily apparent to those killed in the art that functions respectively performed in the signal transceiver 430, the monitoring portion 440, the system controller 450 and the operating portion 460 may be performed in another module. For example, in the foregoing description, the image processor 462 converts an MR signal received in the RF data acquirer 438 into a digital signal. However, this conversion for the digital signal may be directly performed in the RF data acquirer 438 or the RF coil 426.

The gantry 420, the RF coil 426, the signal transceiver 430, the monitoring portion 440, the system controller 450 and the operating portion 460 may be connected to one another wirelessly or by a wire. In the case where they are connected wirelessly, a device (not shown) for synchronizing clocks between them may be additionally needed. Communication among the gantry 420, the RF coil 426, the signal transceiver 430, the monitoring portion 440, the system controller 450 and the operating portion 460 may use a high-speed digital interface such as low voltage differential signaling (LVDS), asynchronous serial communication, such as universal asynchronous receiver transmitter (UART), a low delay network protocol, such as an error synchronous serial communication or controller area network (CAN), or optical communication, or any other communication method that is well known to one of ordinary skill in the art.

Figure 5:
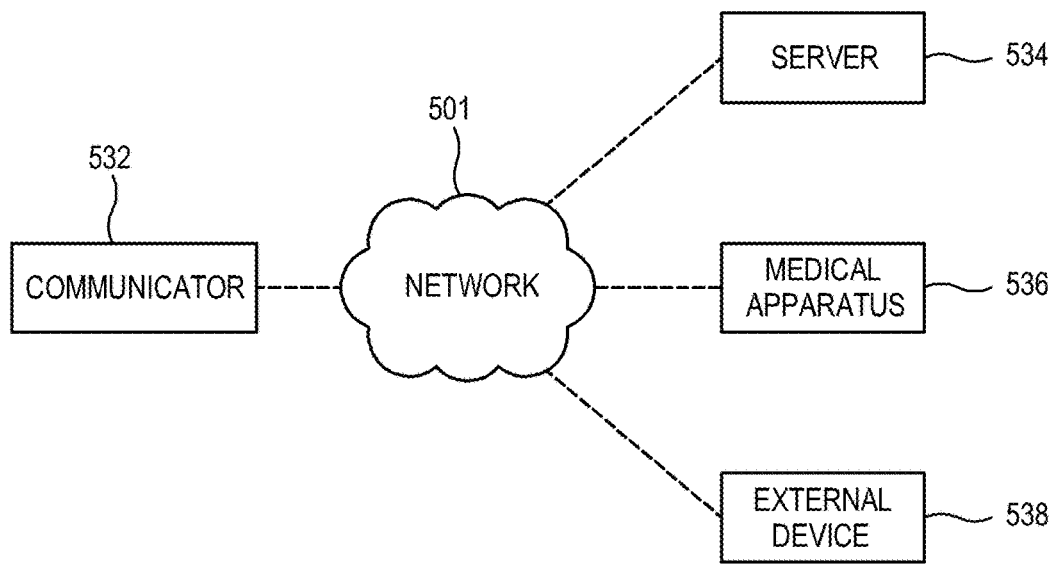
FIG. 5 is a diagram illustrating an example communicator for performing communication with the outside in a network system according to an example embodiment.

FIG. 5 is a diagram illustrating an example communicator (e.g., including communication circuitry) 532 for allowing the image processing apparatus 100 with the MRI apparatus 102 of FIG. 4 to perform communication with the outside in a network system.

The communicator 532 illustrated in FIG. 5 is connectable with at least one among the gantry 420, the signal transceiver 430, the monitoring portion 440, the system controller 450 and the operating portion 460 illustrated in FIG. 4. In other words, the communicator 532 may exchange data with a hospital server or other medical apparatus in a hospital connected through, for example, a picture archiving and communication system (PACS), and perform data communication in accordance with digital imaging and communications in medicine (DICOM) standards.

As illustrated in FIG. 5, the communicator 532 connects with a network 501 by a wire or wirelessly and may include various communication circuitry that performs communication with an external server 534, an external different medical apparatus 536 or an external device 538.

For example, the communicator 532 may transmit and receive data related to diagnosis of an object through the network 501, and may also transmit and receive a medical image scanned by another medical apparatus 536 such as the CT, ultrasound, X-ray and the like apparatus.

According to another example embodiment, the communicator 532 illustrated in FIG. 5 may be included in the CT apparatus 101 of FIG. 2 and FIG. 3. In this case, the communicator 532 illustrated in FIG. 5 is equivalent to the communicator 232 illustrated in FIG. 3. Further, the different medical apparatus 536 may be the MRI apparatus 102 of FIG. 1 or the ultrasound apparatus 103.

Further, the communicator 532 illustrated in FIG. 5 may be included in the MRI apparatus 102 of FIG. 4. In this case, the MRI apparatus 102 illustrated in FIG. 4 may further include the communicator 532 of FIG. 5. In addition, the different medical apparatus 536 may for example be the CT apparatus 101 of FIG. 1 or the ultrasound apparatus 103.

Detailed operations of the communicator 532 are, for example, as follows.

The communicator 532 is connected to the network 501 by a wire or wirelessly and performs communication with the server 534, the external medical apparatus 536 or the external device 538. The communicator 532 may exchange data with a hospital server connected through the picture archiving and communication system (PACS) or another medical apparatus in the hospital.

Further, the communicator 532 may perform data communication with the external device 538 or the like in accordance with digital imaging and communications in medicine (DICOM) standards.

The communicator 532 may transmit and receive an image of an object and/or data related to diagnosis of the object through the network 501. The communicator 532 may receive a medical image or the like obtained in another medical apparatus 536 such as the MRI apparatus 102, the X-ray apparatus, etc.

Further, the communicator 532 may receive a diagnostic history, a treatment schedule or the like of a patient from the server 534 and use them in a clinical diagnosis of the patient. Further, the communicator 532 may perform data communication with not only the server 534 or the medical apparatus 536 in the hospital, but also the external device 538 such as a portable device (terminal) of a user or a patient.

In addition, the communicator 532 may transmit information about whether equipment is normal or abnormal and information about status of quality control to a system manager or a service manager through the network and then get feedback on the information.

According to another example embodiment, the image processing apparatus 100 may be achieved by an ultrasound apparatus 103.

Figure 6:
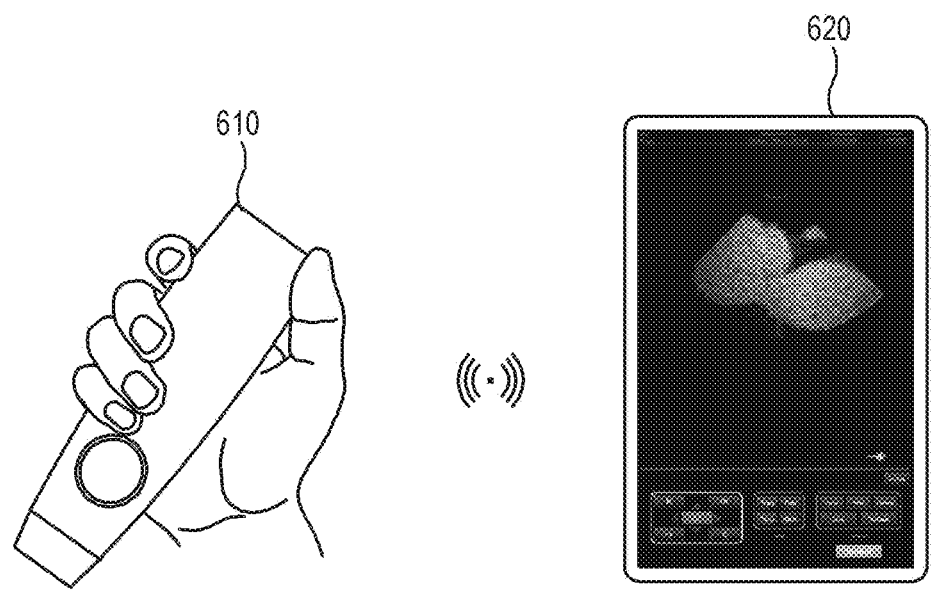
FIG. 6 is a diagram illustrating an example ultrasound apparatus as an image processing apparatus according to an example embodiment.

FIG. 6 is a diagram illustrating an example ultrasound apparatus 103 as an image processing apparatus 100 according to an example embodiment.

As illustrated in FIG. 6, the image processing apparatus 100 may be the ultrasound apparatus (or an ultrasonography machine) 103 that generates an image in real time during an interventional medical procedure.

The ultrasound apparatus 103 transmits an ultrasound signal from a body surface of an object toward a predetermined portion inside a body, and obtains an image of a blood stream or plane-section of a soft tissue based on information about the ultrasound signal reflected from an organ inside the body (hereinafter, referred to as an ultrasound echo signal).

According to an example embodiment, as illustrated in FIG. 6, the ultrasound apparatus 103 gets an ultrasound medical image, and the medical image is provided to a system including a plurality of devices 610 and 620 to display the medical image thereon.

According to an example embodiment, the ultrasound apparatus 103 uses a probe device (hereinafter, referred to as a probe) 610 to emit the ultrasound signal to a region of interest in the object, and detects the reflected ultrasound signal, e.g., the ultrasound echo signal, thereby generating an ultrasound image. The ultrasound image based on the ultrasound echo signal received in the probe device 610 is displayed through a display apparatus 620.

In general, the probe device 610 is connected to a main body of an ultrasound diagnostic apparatus and is in contact with a part of an object to be examined, thereby transmitting and receiving the ultrasound signal to and from the object. According to an example embodiment the probe device 610 may serve not only to transmit and receive the ultrasound signal to and from the object to be examined, but also to generate an image based on the received ultrasound signal. That is, while the existing ultrasonography system is divided into the ultrasound diagnostic main body and the probe, the probe device 610 according to an example embodiment may include only the probe or may include both the existing ultrasound diagnostic main body and the probe.

According to an example embodiment, the ultrasound apparatus 103 may be achieved in various forms. For example, the probe 610 set forth herein may be achieved by not only a stationary terminal but also a mobile terminal. If the probe 610 is the mobile terminal, the display apparatus 620 may include a tablet computer such as a smart pad, a smart TV, a smart phone, a desktop computer, a laptop computer, a personal digital assistant (PDA), a personal portable information terminal, or the like, but is not limited thereto. FIG. 6 illustrates an example that the display apparatus 620 is the tablet computer.

The probe 610 to be in contact with the object may include a plurality of elements (e.g., a transducer) (hereinafter, referred to as a transducer) (not shown) and a light source (not shown). When ultrasonic waves ranging several to hundreds of MHz are transmitted from the probe 610 to a specific region inside a patient's body, the ultrasonic waves are partially reflected from layers between many different tissues. The ultrasonic waves are reflected from anatomical entities changed in density within the body, for example, blood cells in blood plasma, small tissues (e.g., structures) in organs, etc.

The transducer may include various ultrasonic transducers, for example, a piezoelectric ultrasonic transducer using a piezoelectric effect of a piezoelectric material, a capacitive micromachined ultrasonic transducer (cMUT) for conversion between ultrasonic and electric signals based on change in electrostatic capacity, magnetic micromachined ultrasonic transducer (mMUT) for conversion between ultrasonic and electric signals based on change in a magnetic field, an optical ultrasonic detector for conversion between ultrasonic and electric signals based on change in optical characteristics, or the like.

The plurality of elements may include a plurality of piezoelectric elements. The plurality of piezoelectric elements may be formed by dividing the piezoelectric material into a plurality of units. For example, a long piezoelectric transducer material may be diced. However, there are no limits to the method of manufacturing the plurality of piezoelectric elements. For example, there are various methods such as a method of forming a plurality of piezoelectric elements by pressing a piezoelectric material against a metal mold, and so on. The piezoelectric material may include a piezoelectric ceramic, single crystal, a composite piezoelectric material of the material and polymer, or the like causing a piezoelectric phenomenon.

A transducer array includes the piezoelectric element as an element for conversion between the ultrasonic and electric signals, but not limited thereto. That is, various ultrasound transducers are available as described above, and thus the plurality of elements may be variously achieved corresponding to the kinds of ultrasound transducers.

The plurality of elements may be arranged as a straight type (a linear array) or a curved type (a convex array). Further, the plurality of elements may be arranged as a double layer type or a multi-layer type (a phased array). This array may be variously set in accordance with a designer's intention. The plurality of elements having such an array may be covered with a cover.

If the transducer includes the plurality of elements one-dimensionally arranged on a plane perpendicular to a ultrasound traveling direction, it will be called a one-dimensional transducer array. The one-dimensional transducer array may include not only a linear array but a convex array. The one-dimensional transducer array has advantages that it is easily manufactured and costs low.

Further, the plurality of elements for the transducer may be two-dimensionally arranged on a plane perpendicular to the ultrasound traveling direction, and this will be called a two-dimensional transducer array. The two-dimensional transducer array may include a linear array and a convex array.

Here, the two-dimensional transducer array properly delays input time of signals input to the respective elements and thus transmits ultrasound waves to an object along an external scan line, thereby obtaining a 3D image based on a plurality of echo signals. Thus, the two-dimensional transducer array may be easier to form a 3D image.

The probe device 610 may further include a light source (not shown). The light source is to emit light to the inside of the object. For example, the light source may use at least one light source for emitting light having a specific wavelength. Alternatively, the light source may employ a plurality of light sources for emitting light having different wavelengths. The wavelength of the light emitted from the light source may be selected by taking a target in the object into account. Such a light source may be achieved by a laser diode (LD), a light emitting diode (LED), a solid-state laser, a gas laser, an optical fiber, or combination thereof.

The transducer provided in the probe 610 generates a ultrasound signal in accordance with a control signal, and transmits the generated ultrasound signal to the inside of the object. Then, the transducer receives, e.g., detects an ultrasound echo signal reflected from a specific organ (e.g. a lesion) inside the object.

Such reflected ultrasound waves oscillate the transducer of the probe 610, and output electric pulses corresponding to the oscillations of the transducer. These electric pulses are converted into an image. If the anatomical entities are different in characteristic of reflecting the ultrasound waves, the anatomical entities are displayed with different brightness on an ultrasonic image in a brightness (B) mode.

As described above, the medical images obtained by various medical apparatuses represent the object variously based on the kinds and scanning methods of the medical apparatus. Further, the characteristics of the obtained medical image may vary depending on the kinds and scanning methods of medical apparatus. For example, a certain medical image is suitable for detecting cancer tissues, and another medical image is suitable for detecting a blood vessel.

Therefore, an apparatus for providing a medical image has to be used corresponding to a user's intention in consideration of a reading part on an image.

Below, an image processing apparatus according to an example or alternative embodiment, which processes a medical image and provides it to a user so that s/he can easily examine a predetermined region on the medical image, will be described in greater detail with reference to the accompanying drawings.

The image processing apparatus 100 according to an example or alternative embodiment may be any image processing apparatus capable of displaying, storing and/or processing a medical image.

For example, the image processing apparatus 100 according to an example or alternative embodiment may be included in the CT apparatus 101, the MRI apparatus 102, the ultrasound apparatus 103 or the like described in FIG. 2 to FIG. 6. For example, the image processing apparatus 100 may process an obtained medical image and provide it to a user through the display 230, 429 of FIG. 3 or FIG. 5. Further, the image processing apparatus 100 may be the display apparatus 620 included in the ultrasound apparatus 103 of FIG. 6 and receiving an ultrasound image from the probe device 610. In this case, the image processing apparatus 100 may include the communicator 532 described in FIG. 5.

Further, the image processing apparatus 100 according to an example or alternative embodiment may be included in the server 534 or the external device 538 connected to at least one of the medical apparatuses such as the MRI apparatus 102, the CT apparatus 101, the ultrasound apparatus 103, etc. described in FIG. 2 to FIG. 6 through the network 501. Here, the image processing apparatus 100 may be included in the picture archiving and communication system (PACS) that can display, store or process at least one among various medical images.

Further, the image processing apparatus 100 according to an example or alternative embodiment may be included and provided in any medical image apparatus/system capable of processing/reproducing an image based on data acquired by scanning an object besides the CT apparatus 101, the MRI apparatus 102 or the ultrasound apparatus 103, or may be connected to any medical image apparatus/system.

Figure 7:
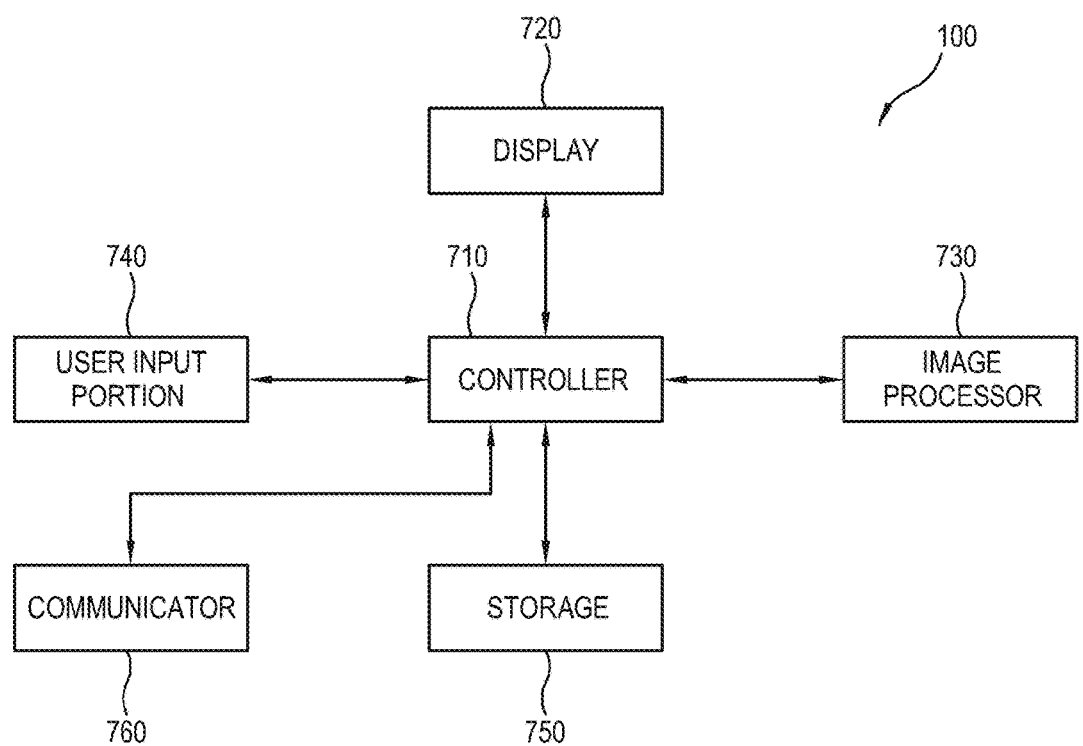
FIG. 7 is a block diagram illustrating an example image processing apparatus according to an example embodiment.

FIG. 7 is a block diagram illustrating an example image processing apparatus 100 according to an example embodiment;

As illustrated in FIG. 7, an image processing apparatus 100 according to an example embodiment includes a controller 710, a display 720, an image processor 730, a user input portion (e.g., including input circuitry) 740, a storage 750 and a communicator (e.g., including communication circuitry) 760. However, all the elements illustrated therein may be not necessary, and other general-purpose elements may be added in addition to the illustrated elements.

If the image processing apparatus 100 is included in the CT apparatus 101 illustrated in FIG. 2 and FIG. 3, the controller 710, the display 720, the image processor 730, the user input portion 740 and the storage 750 may be respectively equivalent to the controller 218, the display 230, the image processor 226, the user input portion 228 and the storage 224 of FIG. 3. Therefore, in terms of the image processing apparatus 100, repetitive descriptions to those of FIG. 2 or FIG. 3 will be avoided.

Further, if the image processing apparatus 100 is included in the MRI apparatus 102 illustrated in FIG. 4, at least a portion of the image processing apparatus 100 may be equivalent to the operating portion 460. For example, the image processor 730 and the display 720 may respectively correspond to those of the image processor 462 and the output portion 464 of FIG. 4. The controller 710 may correspond to at least a portion of the operating portion 460 and/or the display controller 448. Therefore, in terms of the image processing apparatus 100, repetitive descriptions to those of FIG. 4 will be avoided.

Further, the image processing apparatus 100 may be included in one among the server 534, the medical apparatus 536 and the external device 538 described in FIG. 5 and the ultrasound apparatus 103 described in FIG. 6.

The display 720 displays an application related to an operation of the image processing apparatus 100. For example, the display 720 may display a menu, a guideline or the like needed in making a diagnosis using the medical apparatus. Further, the display 720 may display images acquired while making a diagnosis, and a user interface (UI) for allowing a user to control a medical image processing apparatus.

FIG. 7 illustrates an example in which the image processing apparatus 100 includes only one display 720, but not limited thereto. The image processing apparatus may be configured to include a plurality of displays, e.g. a main display and a sub display.

In this example embodiment, the display 720 displays a first image (e.g., a first medical image) obtained by scanning an object involving at least one anatomical entity and/or a third image (e.g., a third medical image) for providing information about condition of a predetermined anatomical entity, e.g., diagnostic information based on object information measured from a region corresponding to the anatomical entity of the first image and standard information stored in the storage 750. Here, the object information and the standard information may be anatomical information, and the diagnostic information may be functional information.

The display 720 may further display a second image (e.g., a second medical image) defined as a reference image used while generating the third image of providing the diagnostic information.

Here, the first image is a medical image obtained by photographing an object, which may include a CT image, an MRI image or the like tomography image, and an X-ray image, an ultrasound image or the like medical image scanned for making a disease diagnosis.

The image processor 730 processes an image to be displayed on the display 720. For example, the image processor 730 processes a signal obtained by scanning the object into image data to be displayable on the display 720.

An imaging method for the medical image includes a method of scanning an object by emitting a ray such as an X-ray to the object like the imaging method for an X-ray image. This method is an imaging method for an object regardless of a photographing technique or a scan mode. Further, this method is possible to form an image of an object directly without any separate restoration or calculation for the image desired to be acquired.

The photographing technique or scan mode is variously used in scanning an object like an MRI or CT image to thereby form an image of an object. In this second method, many variables to be taken into account when an object is scanned are used, and it is thus possible to obtain images different in characteristic even though one part of a body is scanned. In other words, the scan mode is changed based on use or purposes and it is thus possible to obtain an image for the purpose. Further, this method may include separate restoration or calculation for an image desired to be obtained, thereby acquiring the desired image.

Here, the technique used in obtaining a medical image by scanning an object is called a 'scan protocol' or a 'protocol'. Further, the image processor 730 applies a predetermined protocol to the obtained image data, thereby generating a medical image.

According to an example embodiment the image processor 730 may generate a calculated or post-processed image data (e.g., the second or third image) based on image data (e.g., the first image) obtained by the protocol. In this embodiment, the calculation or post-processing process may include image analysis, entity segmentation, length/volume measurement and pixel count of segmented entities, unit conversion, calculation (e.g., determination) of an index indicating information about condition of an entity, or the like, but is not limited thereto.

In case of the CT apparatus 101, different protocols are applied based on whether contrast media is administered, thereby scanning an object. Further, image data acquired in case of the CT apparatus 101 may be a sonogram or projection data, and the acquired scan data may be used to generate image data, e.g., the first image.

In case of the MRI apparatus 102, various protocols are applied to scan an object, and thus an MR signal is acquired and used to generate an image of the object. Below, the data acquired by scanning the object, for example, the MR signal or K-space data will be referred to as scan data, and an image of the object generated based on the scan data will be called image data. The image data is equivalent to the foregoing first image.

The user input portion 740 is provided to receive a command from a user. The image processing apparatus 100 in this embodiment receives a user's input for controlling the image processing apparatus 100 through the user input portion 740, and displays the acquired first medical image, second medical image and/or third medical image through the display 720 in response to the user's input.

The user input portion 740 may include various input circuitry, such as, for example, and without limitation, a button, a key pad, a switch, a dial or a user interface displayed on the display 720 to thereby allow a user to directly control the image processing apparatus 100. According to an example embodiment the user input portion 740 may include a touch screen provided on the display 720. If the user input portion 740 includes the touch screen, the display 720 may provide information about an entity corresponding to a point selected by a user on the displayed medical image or may enlarge the selected point.

The storage 750 stores data under control of the controller 710. The storage 750 may, for example, be achieved by a flash memory, a hard-disc drive and the like nonvolatile storage medium. The storage 750 is accessed by the controller 710, and thus the controller 710 can perform reading/writing/modifying/deleting/updating/etc. with regard to the data in the storage 750.

The data stored in the storage 750 may for example include not only an operating system for driving the image processing apparatus 100 but also various applications executable on this operating system, image data, auxiliary data, etc.

In this example embodiment, the storage 750 may store various pieces of data for providing information about a predetermined anatomical entity. For example, the storage 750 stores at least one piece of image data generated by applying at least one protocol in the image processing apparatus 100 and/or at least one piece of medical image data received from the outside. The image data stored in the storage 750 is displayable on the display 750. Further, the image data stored in the storage 750 is included in the first medical data according to an example embodiment.

Further, the storage 750 may store standard information about at least one anatomical entity. This standard information may be utilized in estimating volume of a predetermined anatomical entity (e.g. a lung) at a predetermined time (the maximum inspiration or the maximum expiration) to be described later. The standard information stored in the storage 750 may be sorted by at least one of age, sex, height, weight and race of a patient.

The communicator 760 includes a wired/wireless network communication module including various communication circuitry for performing communication with various external devices. The communicator 760 sends a command/data/information/signal received from the external device to the controller 710. Further, the communicator 760 sends a command/data/information/signal received from the controller 710 to the external device.

The communicator 760 in this embodiment may be provided inside the image processing apparatus 100, but not limited thereto. The communicator may be achieved in the form of a dongle or module, and detachably connected to a connector (not shown) of the image processing apparatus 100.

According to another example embodiment, the communicator 760 may include various communication circuitry, such as, for example, and without limitation, an input/output (I/O) port for connecting with a human interface device (HID). The image processing apparatus 100 may transmit and receive image data to and from an external device through the I/O port.

In this embodiment, the communicator 760 may receive the medical image data generated in a different medical apparatus. Here, the different medical apparatus may include various kinds of medical apparatus. For example, the different medical apparatus may be the CT apparatus. As necessary, the different medical apparatus may be the MRI apparatus or the ultrasound apparatus.

According to an example embodiment, the image processing apparatus 100 may directly connect with the different medical apparatus via the communicator 760. The communicator 760 may include a connector for connection with an external storage medium where a medical image is stored.

The controller 710 may include various processing circuitry and performs control operations for various elements of the image processing apparatus 100. For example, the controller 710 performs processes related to image processing/entity segment/volume estimation, etc. processed by the image processor 730, and control operations corresponding to a command from a user input portion 740, thereby controlling the general operations of the image processing apparatus 100.

The controller 710 includes at least one processor. The at least one processor loads a program from a nonvolatile memory (e.g. ROM) to a volatile memory (e.g. RAM) and executes the program.

The controller 710 in this embodiment includes at least one general-purpose processor such as a central processing unit (CPU), an application processor (AP), a microcomputer (MICOM), or the like, loads a program corresponding to a predetermined algorithm stored in the ROM to the RAM, and executes the program, thereby controlling various operations of the image processing apparatus 100.

If the controller 710 of the image processing apparatus 100 is achieved by a single processor, e.g. a CPU, the CPU may be provided to execute various functions to be implemented in the image processing apparatus 100, for example, selection of a protocol and control of a corresponding image as various imaging processes for forming a medical image to be displayed on the display 720, response to a command received through the user input portion 740, control of wired/wireless network communication with an external device, etc.

The processor may include a single core, a dual core, a triple core, a quad core and the like multiple core. The processor may include a plurality of the processor, for example, a main processor and a sub processor. The sub processor is provided to operate in a standby mode (hereinafter, referred to as a sleep mode) where only standby power is supplied and the image processing apparatus 100 does not operate.

The processor, the ROM and the RAM included in the controller 710 may be connected through an internal bus.

According to an example embodiment if the image processing apparatus 100 is a laptop or desktop computer, the controller 710 is provided in the main body and further includes a graphic processing unit (not shown) for processing an image. If the image processing apparatus 100 is a portable terminal such as a smart phone, a smart pad, etc., the processor may include a GPU, for example in such a manner that the processor is provided as a system on chip (SoC) of combining the core and the GPU.

In addition, the controller 710 may include a specific function supported in the image processing apparatus 100, and may for example include a program for performing a function of sensing an error in a predetermined element including the main processor, and a chip, e.g., an integrated circuit (IC) provided as a processor dedicated for executing the program.

According to an example embodiment, the controller 710 may be a platform capable of analyzing the medical image through the user input portion 740 or making a diagnosis through the analyzed medical image, and receive a user command for executing a predetermined application. The executed application may include an input region where various buttons are displayed as a UI selectable by a user, and a display region where the medical image is displayed.

Thus, a user can load the medical image stored internally or externally through the UI in the input region of the application, and the loaded medical image is displayed on the display 720 through the display region of the application. Further, a user may input a command to receive information about a predetermined anatomical entity through the executed application.

According to an example embodiment the image processor 730 may be achieved by software, e.g., a medical image analyzing application to be driven by hardware, e.g., the controller 710 including at least one processor.

That is, the following operations of the image processor 730 are implemented by executing software to be driven by the controller 710. Therefore, various operations to be performed by the image processor 730 may be implemented by the controller 720, e.g., by at least one processor.

The controller 710 of the image processing apparatus 100 according to an example embodiment detects a region corresponding to a plurality of anatomical entities with respect to the first medical image obtained by scanning an object including the plurality of anatomical entities. The controller 710 estimates a volume of a first anatomical entity included in the object based on the standard information stored in the storage 750 and the object information measured from the region of the detected anatomical entity. Further, the controller 710 may provide information about condition of the first anatomical entity based on the estimated volume. Here, the estimated volume corresponds to the size of the first anatomical entity (e.g., the lung) as the anatomical volume, and it is thus possible to provide functional information about the condition of the first anatomical entity based on the estimated volume.

The object is the whole or partial body of a patient, for example, a chest. According to an example embodiment, a medical image obtained by scanning the object may be a chest image, and more specifically a CT image of a lung. The lung CT image may include the plurality of anatomical entities such as a lung, a diaphragm and a rib cage with ribs.

Below, it will be described in greater detail that information about condition of a lung defined as the first anatomical entity (e.g., diagnostic information) is provided based on the medical image of the chest image, e.g., the lung CT image. Here, the information about the diaphragm and the rib cage, e.g., the organs surrounding the first anatomical entity, e.g., the lung may be used, and the diaphragm and the rib cage (or ribs) are defined as the second anatomical entity and the third anatomical entity, respectively.

The following descriptions are merely an example of example embodiments, and do not limit the present disclosure. For example, the image processing apparatus 100 according to an example embodiment may be achieved to provide information about condition of a predetermined anatomical entity such as a lung through the MRI image as well as the CT image. Further, the anatomical entity targeted for providing the information is not limited to the lung, and may be used in making a diagnosis of stomach, heart, brain and the like organs or muscle and the like tissue.

According to an example embodiment the image processing apparatus 100 estimates a volume of a lung at a predetermined point in time, e.g., at the maximum inspiration or the maximum expiration through the CT image of the scanned lung, and provides diagnostic information about the lung based on the estimated volume. Here, the lung CT image may be an image taken by the CT apparatus, or an image taken in the past for another diagnostic purpose. The lung CT image includes an inspiratory (or inhale) image and an expulsive (or exhale) image.

According to an example embodiment the image processing apparatus 100 may employ an inspiratory image to estimate a lung volume at the maximum inspiration, and employs an expiratory image to estimate a lung volume at the maximum expiration. In addition, the image processing apparatus 100 determines indexes (TLC, VC, RV) of providing information about condition of a lung at the maximum inspiration and the maximum expiration based on the information about the estimated lung volume, measurement values of the lung CT image (e.g., object information), and previously stored standard values (e.g., standard information).

According to another example embodiment the image processing apparatus 100 estimates a lung volume at the maximum inspiration based on an inspiratory image. In addition, the image processing apparatus 100 determines indexes (TLC, VC) of providing information about condition of a lung at the maximum inspiration based on the information about the estimated lung volume, measurement values of the lung CT image (e.g., object information), and previously stored standard values (e.g., standard information), and determines an index (RV) of providing information about condition of a lung at the maximum expiration based on the determined indexes (TLC, VC).

That is, the image processing apparatus 100 according to this example embodiment employs at least one of the inspiratory image and the expiratory image to provide information about condition of a lung.

Figure 8:
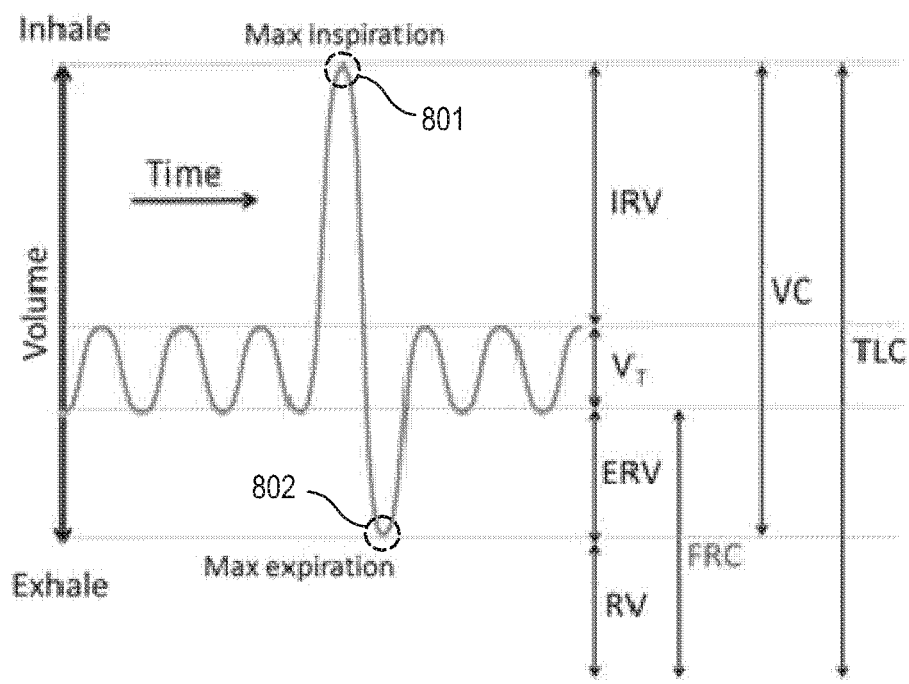
FIG. 8 is a graph illustrating example lung-disease diagnostics based on spirometry.
Figure 9:
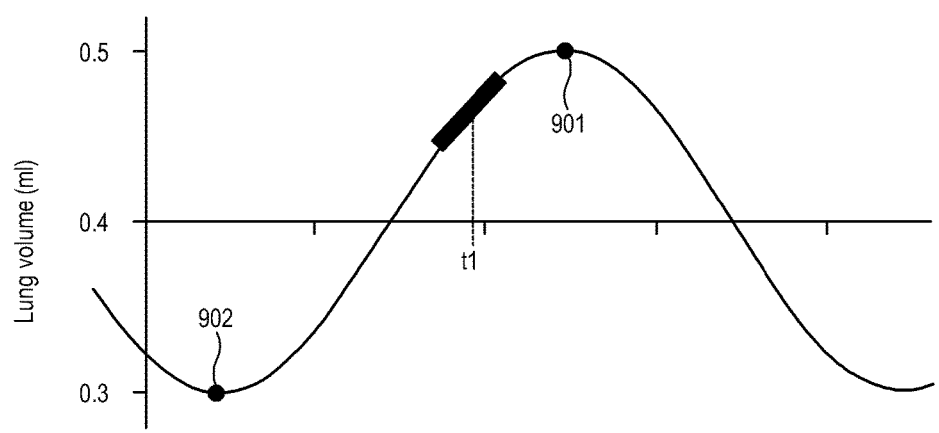
FIG. 9 is a graph illustrating example variation in a lung volume depending on a respiration cycle.

FIG. 8 is a graph illustrating example lung-disease diagnostics based on spirometry, and FIG. 9 is a graph illustrating example variation in a lung volume depending on a respiration cycle.

As illustrated in FIG. 8, in a general vital capacity measuring (spirometry) method, time of the maximum inspiration 801 or the maximum expiration 802 of a patient is specified in measurement result data, various indexes (IRV, ERV, RV, FRC, VC, TLC, etc.) at the corresponding time are employed is making the lung-disease diagnostics However, it is impossible for a patient to continuously keep the condition of the maximum inspiration or expiration while taking a lung CT image, and it is also very difficult to control a CT image to be taken in sync with the time of a patient's maximum inspiration or expiration.

Therefore, the image processing apparatus 100 according to an example embodiment estimates information about a lung at the maximum inspiration (Max. inspiration) 901 or the maximum expiration (Max. expiration) 902 based on the lung CT image taken at a random time t1 as shown in FIG. 9, and utilizes the estimated information in making a diagnosis of a lung.

FIGS. 10, 11, 12, 13, 14 and 15 are diagrams illustrating example processes that the image processing apparatus 100 according to an example embodiment offers information about conditions of a predetermined anatomical entity.

The controller 710 detects a region corresponding to an anatomical entity targeted to be examined from a lung CT image (e.g., the first medical image) including a plurality of anatomical entities. The targeted anatomical entity includes not only internal organs or viscera but also various tissues such as muscles or the like.

Figure 10:
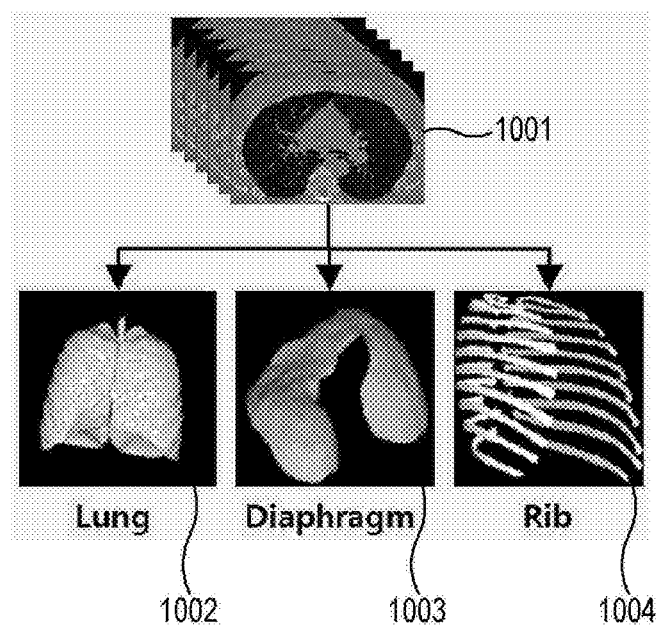
FIGS. 10, 11, 12, 13, 14 and FIG. 15 are diagrams illustrating example processes in which an image processing apparatus according to an example embodiment offers information about conditions of a predetermined anatomical entity.

In this process, as illustrated in FIG. 10, the controller 710 detects regions respectively corresponding to the plurality of anatomical entities included in a first medical image 1001, and segments the first medical image according to the detected regions.

FIG. 10 illustrates an example that the regions respectively corresponding to a lung, a diaphragm and a rib are detected and segmented from the lung CT image. Here, the lung, the diaphragm and the ribs may be respectively defined as the first anatomical entity, the second anatomical entity, the third anatomical entity.

The controller 710 may display images 1002, 1003, 1004 segmented based on the regions of the respective anatomical entities as a second image on the display 720.

The controller 710 measures the length or volume of the relevant anatomical entity in the region of each anatomical entity. According to an example embodiment the controller 710 may measure the length of the diaphragm, e.g., the second anatomical entity as a first measurement value ($L_{Di}$), the volume of the lung, e.g., the first anatomical entity as a second measurement value ($L_N$), and the diameter of the rib cage of the ribs, e.g., the third anatomical entity as a third measurement value ($D_{NC}$).

The foregoing measurement values ($L_N$, $L_{DI}$, $D_{NC}$) may be utilized in estimating the volume of the lung, e.g., the first anatomical entity at a predetermined time (at the maximum inspiration or the maximum expiration). According to an example embodiment the measurement value measured from the medical image is defined as the object information. If the first medical image is the inspiratory image, the object information is utilized in estimating the volume of the lung at the maximum inspiration. Further, if the first medical image is the expiratory image, the object information is utilized in estimating the volume of the lung at the maximum expiration.

For example, the controller 710 employs the object information, e.g., the first measurement value ($L_{DI}$) of the diaphragm, e.g., the second anatomical entity in order to estimate the maximum diameter of the rib cage in the ribs, e.g., the third anatomical entity ($D_{RC}$). Here, the maximum diameter of the rib cage is defined as a first estimated value, and the standard information stored in the storage 750 may be used in this procedure.

According to an example embodiment the standard information stored in the storage 750 is to estimate a first estimated value corresponding to the first measurement value ($L_{DI}$), e.g., estimate the maximum diameter of the rib cage ($D_{RC}$). For example, the storage 750 may be previously stored with standard information for a standard table where relationships between the first measurement value ($L_{DI}$) and the first estimated value ($D_{RC}$) are tabulated.

Figure 11:
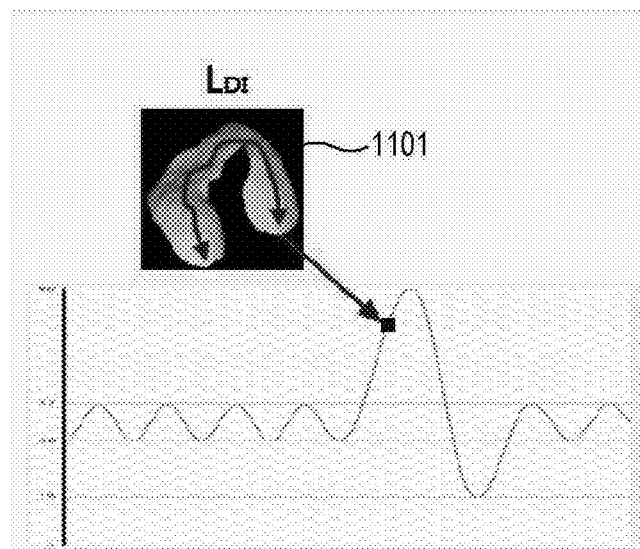
Figure 12:
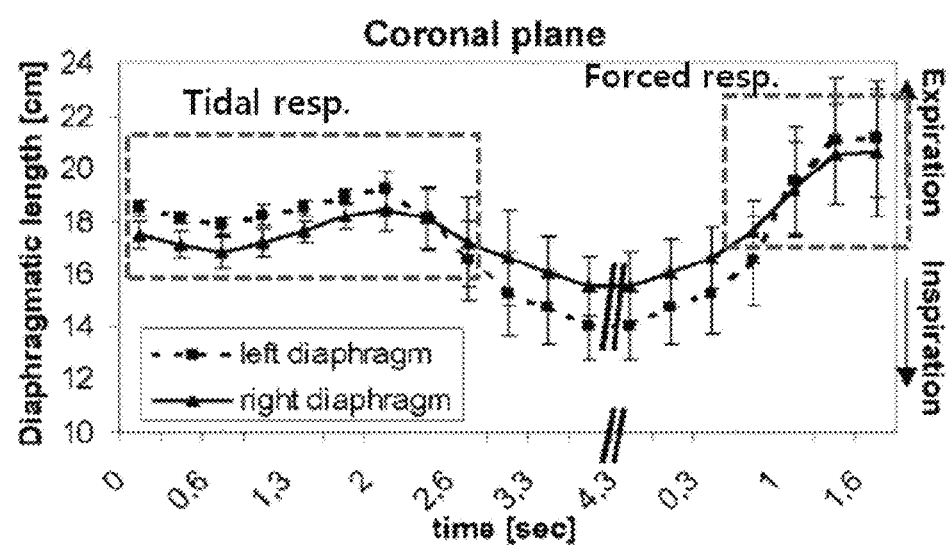
Figure 13:
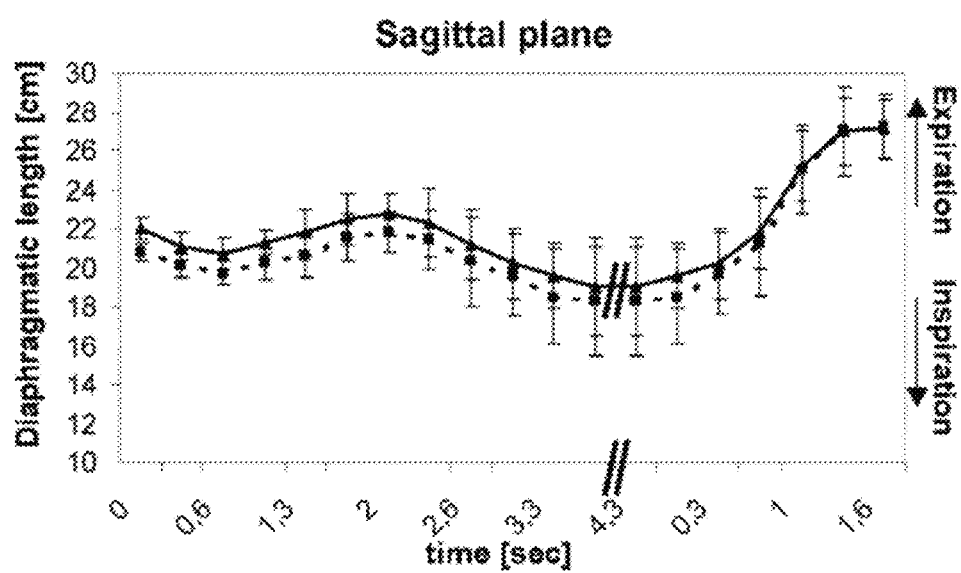

Referring to FIG. 11, the controller 710 can estimate the current respiration condition when the lung CT image 1101 is taken, based on the first measurement value ($L_{DI}$) corresponding to the length of the diaphragm at a random point in time. FIG. 12 and FIG. 13 illustrate diaphragmatic lengths according to respiration cycles by way of example.

The image processing apparatus 100 according to an example embodiment estimates an anatomical volume of a lung at the maximum inspiration or the maximum expiration, based on a relationship between the diaphragm, e.g., the muscle and the chest cavity.

The standard table stored in the storage 750 includes a relationship between the length of the diaphragm ($L_{DI}$) and the maximum size of the rib cage ($D_{RC}$). By way of example, the following Table 1 shows regression equations relating Lzapp to $L_{DI}$ and $D_{RC}$ according to subjects of persons to be examined (or patients) sorted with respect to a predetermined reference at the expulsive and inspiratory time. Here, Lzapp refers to a length of zone of apposition of the diaphragm.

TABLE 1

|  |  | Regression | R2 |
|---|---|---|---|
| Expulsive | Subject 1 | Lzapp = −128 + 0.464 × LDI | 0.624** |
|  |  | Lzapp = 30 − 0.059 × DRC | 0.004 |
|  | Subject 2 | Lzapp = −235 + 0.742 × LDI | 0.419** |
|  |  | Lzapp = 304 − 1.069 × DRC | 0.532** |
| Inspiratory | Subject 1 | Lzapp = −318 + 1.004 × LDI | 0.887** |
|  |  | Lzapp = 244 − 0.826 × DRC | 0.804** |

TABLE 1-continued

|  | Regression | R2 |
|---|---|---|
| Subject 2 | Lzapp = −123 + 0.400 × LDI | 0.780** |
|  | Lzapp = 282 − 1.031 × DRC | 0.156* |

Lzapp = length of zone of apposition of the diaphragm;
LDI = length of the diaphragm (anteroposterior projection);
DRC = maximal diameter of the rib cage (anteroposterior projection). All values in mm.
*p < 0.05;
**p < 0.001.

Based on the relationship between Lzapp and $L_{DI}$ and the relationship between Lzapp and $D_{RC}$ tabulated in the Table 1, a relationship between $L_{DI}$ and $D_{RC}$ is obtained by the following Equation 1.

$$D_{RC} = \frac{\alpha - \beta * L_{DI}}{\gamma} \quad \text{[Equation 1]}$$

Here, α, β and γ are standard values determined based on the Table 1 according to a subject to which a person to be examined belongs (hereinafter, referred to as a standard subject. Referring to the subject 1 at the expulsive (expiratory) time of the Table 1, α=125, β=0.464 and γ=0.059, and Equation 1 becomes the following Equation 2.

$$D_{RC1} = \frac{158 - 0.464 * L_{DI1}}{0.059} \quad \text{[Equation 2]}$$

In result, the maximum diameter of the rib cage at the expiratory time, e.g., the rib cage ($D_{RC1}$) at the maximum expiration of a person-to-be-examined sorted into the subject 1 is obtained by the Equation 2. Likewise, α=562, β=1.004 and γ=0.826 are determined with respect to the person-to-be-examined sorted into the subject 1 at the maximum inspiration, and thus the rib cage ($D_{RC2}$) is obtained by the following Equation 3.

$$D_{RC2} = \frac{562 - 1.004 * L_{DI2}}{0.826} \quad \text{[Equation 3]}$$

Here, the standard subject may be for example sorted according to at least one of age, sex, height, weight and race. The controller 710 determines each size of rib cage ($D_{RC}$) at the maximum inspiration and the maximum expiration with respect to the standard subject to which a patent belongs among the standard subjects (subject 1, subject 2, . . . , subject N) by the Equation 1 created based on the Table 1. If a patient belongs to the subject 1, at least one of the Equation 2 and Equation 3 is used.

Figure 14:
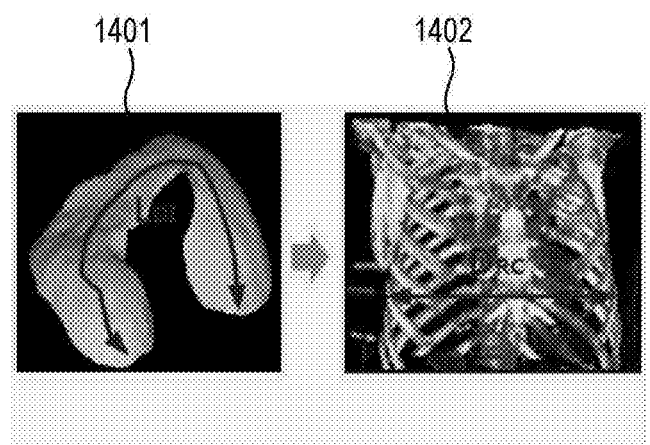

According to the foregoing example embodiments, the controller 710 employs the Equation 1 created based on the standard information stored in the storage 750 to determine a first estimation value ($D_{RC}$) at a predetermined time (e.g. the maximum inspiration or the maximum expiration) corresponding to the first measurement value ($L_{DI}$) 1401 of an object, e.g., a patient as illustrated in FIG. 14. $D_{RC}$ 1402 may be measured as illustrated in FIG. 14.

The controller 710 determines the volume of the lung (Lm) at a corresponding time (e.g. the maximum inspiration or the maximum expiration) from the determined first estimation value (Drc) by the following Equation 4. Here, the volume of the lung (Lm) at the maximum inspiration or the maximum expiration is defined as a second estimation value, and the foregoing second measurement value (Ln) and measurement value (Dnc) may be used together.

$$L_M:L_N=D_{RC}:D_{NC} \quad \text{[Equation 4]}$$

That is, the second estimation value determined by the Equation 4, e.g., the volume of the lung ($L_M$) at the maximum inspiration or the maximum expiration is obtained by the following Equation 5.

$$L_M = \frac{D_{RC} * L_N}{D_{NC}} \quad \text{[Equation 5]}$$

Figure 15:
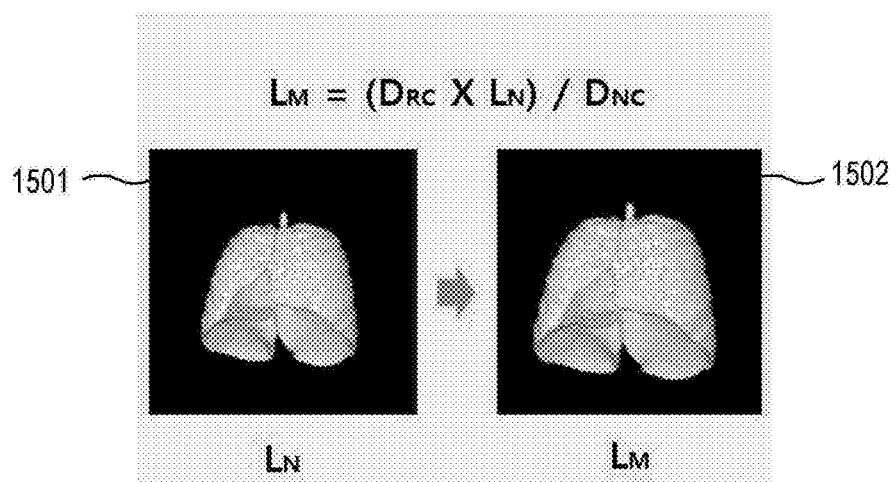

Therefore, as illustrated in FIG. 15, the image processing apparatus 100 according to an example embodiment determines and estimates the volume of the lung ($L_M$) at the maximum inspiration 1502 or the maximum expiration base on the second measurement value ($L_N$) 1501, e.g., the volume of the lung measured at a point in time when the first medical image is taken. In addition, the controller 710 may control the image processor 730 to display an image with the lung corresponding to the estimated volume as the third medical image 1502 on the display 720.

The controller 710 may count the number of pixels in the first medical image, and determine at least one index for offering (functional) information about condition of the first anatomical entity at a point in time when the image is taken. Here, the determined index may for example include at least one of total lung capacity (TLC), vital capacity (VC) and residual volume (RV) as an index used in examining the function of the first anatomical entity, e.g., the lung.

For example, the controller 710 may calculate each of total lung capacity ($TLC_{pixels}$) vital capacity ($VC_{pixels}$) and residual volume ($RV_{pixels}$) at a point in time when the first medical image is taken, in such a manner that pixels are counted by the following Equations 6, 7 and 8. Here, the controller 710 can count pixels of each index, e.g., TLC, VC and RV based on density of an image, in a housefield unit (HU).

$$TLC_{pixels}=\Sigma TLC_{pixel} \quad \text{[Equation 6]}$$

Here, $TLC_{pixel}$ refers to pixels, of which a value (e.g., a CT image value) is present within a range of −1000 HU to −150 HU, among pixels included in the first image.

$$VC_{pixels}=\Sigma VC_{pixel} \quad \text{[Equation 7]}$$

Here, $VC_{pixel}$ refers to pixels, of which a value is present within a range of −910 HU to −800 HU, among pixels included in the first image.

$$RV_{pixels}=\Sigma RV_{pixel} \quad \text{[Equation 8]}$$

Here, $RV_{pixel}$ refers to pixels, of which a value is present within a range of −1000 HU to −450 HU, among pixels included in the first image.

In general, TLC=VC+RV, and therefore the number of pixels in the residual volume ($RV_{pixels}$) may be calculated by the following Equation 9.

$$RV_{pixels}=TLC_{pixels}VC_{pixels} \quad \text{[Equation 9]}$$

The controller 710 converts the counted image sizes (pixels) of total lung capacity ($TLC_{pixels}$), vital capacity ($VC_{pixels}$) and residual volume ($RV_{pixels}$) at the image taking time into volume (ml). The controller 710 may convert total lung capacity ($TLC_{temp}$), vital capacity ($VC_{temp}$) and residual volume ($RV_{temp}$) at the image taking time by the following Equations 10, 11 and 12.

$$TLC_{temp}=TLC_{pixels}*x \text{ resolution}*y \text{ resolution}*z \text{ resolution} \quad \text{[Equation 10]}$$

Here, $TLC_{temp}$ refers to the total lung capacity converted into a unit of volume, which can be obtained by multiplying the image size of total lung capacity ($TLC_{pixels}$) and the resolutions in the x, y and z directions as shown in the Equation 10.

$$VC_{temp}=VC_{pixels}*x \text{ resolution}*y \text{ resolution}*z \text{ resolution} \quad \text{[Equation 11]}$$

Here, $VC_{temp}$ refers to the vital capacity converted into a unit of volume, which can be obtained by multiplying the image size of vital capacity ($VC_{pixels}$) and the resolutions in the x, y and z directions as shown in the Equation 11.

$$RV_{temp}=RV_{pixels}*x \text{ resolution}*y \text{ resolution}*z \text{ resolution} \quad \text{[Equation 12]}$$

Here, $RV_{temp}$ refers to the residual volume converted into a unit of volume, which can be obtained by multiplying the image size of residual volume ($RV_{pixels}$) and the resolutions in the x, y and z directions as shown in the Equation 12.

In addition, the controller 710 may determine indexes, e.g., total lung capacity (TLC), vital capacity (VC) and residual volume (RV), of offering information about condition of a lung, e.g., the first anatomical entity at the maximum inspiration or the maximum expiration, by respectively applying the second measurement values, e.g., the volume of the lung ($L_N$), the second estimation value, e.g., the volume of the lung ($L_M$) at the maximum inspiration or the maximum expiration, and total lung capacity ($TLC_{temp}$), vital capacity ($VC_{temp}$) and residual volume ($RV_{temp}$) converted in a unit of volume to the following Equations 13, 15 and 15.

$$L_M:L_N = TLC:TLC_{temp} \therefore TLC = \frac{L_M * TLC_{temp}}{L_N} \quad \text{[Equation 13]}$$

$$L_M:L_N = VC:VC_{temp} \therefore VC = \frac{L_M * VC_{temp}}{L_N} \quad \text{[Equation 14]}$$

$$L_M:L_N = RV:RV_{temp} \therefore RV = \frac{L_M * RV_{temp}}{L_N} \quad \text{[Equation 15]}$$

Here, TLC=VC+RV, and therefore residual volume (RV) is calculated by the following Equation 16.

$$RV=TLC-VC \quad \text{[Equation 16]}$$

In the foregoing example embodiment, the controller 710 may not determine total lung capacity (TLC), vital capacity (VC) and residual volume (RV) with respect to both the maximum inspiration and the maximum expiration.

For example, the controller 710 uses the Equation 3 and the Equation 5 to estimate the volume of the lung (LM) at the maximum inspiration with respect to a predetermined subject (e.g. the subject 1), and uses the estimation values to determine total lung capacity (TLC) and vital capacity (VC) by the Equations 13 and 14 and the residual volume (RV) by the Equation 16.

The Equation 2 and the Equation 5 may be used to estimate the volume of the lung ($L_M$) at the maximum expiration with respect to a predetermined subject (subject 1), and the estimation values may be used to calculate the residual volume (RV) by the Equation 15.

According to another example embodiment, the volume of the lung ($L_M$) at the maximum inspiration or expiration estimated by the Equation 5 may be used to directly determine the index of offering the condition information of the lung.

For example, the controller 710 may determine at least one of the indexes (TLC, VC and RV) directly from the lung volume of a third medical image 1502 formed as illustrated in FIG. 15.

For example, the controller 710 determines TLC corresponding to a total of pixels satisfying −100 HU<TLC<−400 HU in the maximum inspiration image, and determines VC corresponding to a total of pixels satisfying −950 HU< VC<−850 HU in the maximum inspiration image. Likewise, the controller 710 determines RV by the equation of RC=TLC−VC or a total of pixels satisfying −1000 HU<RV<−600 HU in the maximum expiration image.

In the foregoing example embodiments, the controller 710 of the image processing apparatus 100 uses the medical image taken randomly to estimate total lung capacity (TLC), vital capacity (VC) and residual volume (RV) at a predetermined point in time, e.g., at the maximum inspiration or the maximum expiration. Here, the controller 710 provides information about the estimated total lung capacity (TLC), vital capacity (VC) and residual volume (RV) through the display 720, and thus a doctor or the like user uses this information in making lung disease diagnostics.

Accordingly, it is possible to provide information about lung condition needed for making a diagnosis without using the spirometry. As compared with the spirometry, more various indexes, for example, residual volume (RV), are measured and it is thus possible to make a more correct diagnosis of a lung disease.

Below, an image processing method according to an example embodiment will be described with reference to the accompanying drawings.

Figure 16:
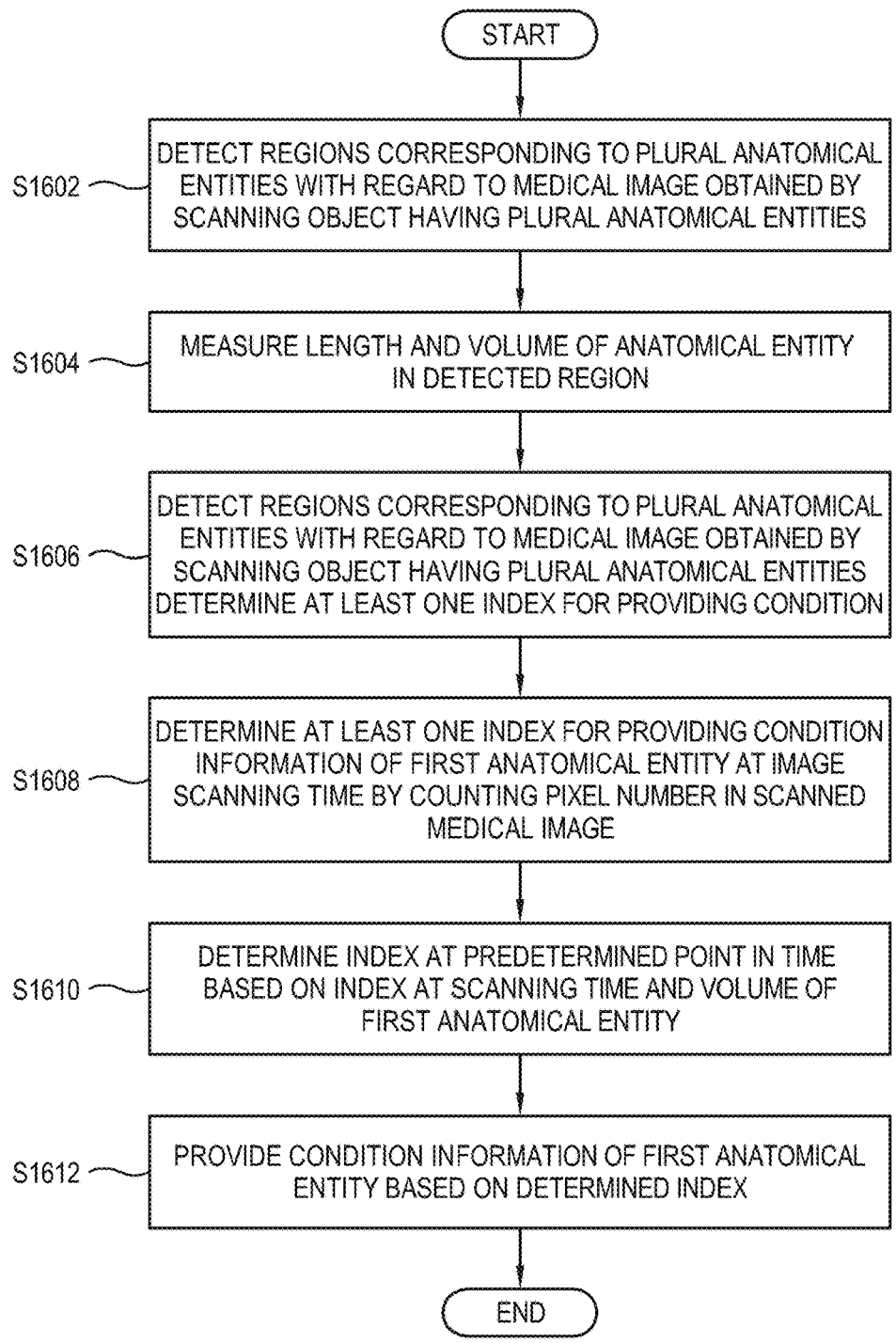
FIG. 16 is a flowchart illustrating an example image processing method according to an example embodiment.

FIG. 16 is a flowchart illustrating an example image processing method according to an example embodiment.

As illustrated in FIG. 16, the controller 710 of the image processing apparatus 100 detects regions corresponding to a plurality of anatomical entities with regard to a medical image 1001 (e.g. a chest CT image including a lung, a diaphragm and ribs) taken by scanning an object including the plurality of anatomical entities (S1602). Here, the controller 710 controls the image processor 730 to use a predetermined image processing process to selectively segment the regions according to the plurality of anatomical entities, and controls the display 729 to display images 1002, 1003 and 1004 corresponding to the segmented regions.

The controller 710 measures the lengths or volumes of the plurality of anatomical entities (e.g. the lung, the diaphragm and the ribs) detected in the operation S1602 (S1604). Here, the measured length or volume of the entity is the measurement value of when the medical image is taken. For example, the length of the diaphragm ($L_{DI}$), the volume of the lung ($L_N$) and the diameter of rib cage ($D_{NC}$) may be measured respectively.

The controller 710 estimates the volume ($L_M$) of the lung, e.g., the first anatomical entity at predetermined point in time (e.g. at the maximum inspiration or the maximum expiration) based on the object information measured in the operation S1604 and the standard information previously stored in the storage 750 (S1606). Here, the controller 710 determines the diameter of the rib cage ($D_{RC}$) at the maximum inspiration or the maximum expiration corresponding to the length of the diaphragm ($L_{DI}$) measured in the operation S1604 based on the standard information, and determines, e.g., estimates the volume of the lung ($L_M$) at the maximum inspiration or the maximum expiration based on the determined diameter of the rib cage ($D_{RC}$) at the maximum inspiration or the maximum expiration and a relationship between the diameter of the rib cage ($D_{NC}$) and the volume of the lung ($L_N$) of when the measured image is taken in the operation S1604.

Further, the controller 710 counts the number of pixels in the medical image taken in the operation S1602, and determines at least one of indexes (e.g. total lung capacity (TLC), vital capacity (VC) and residual volume (RV)) for offering the condition information of the lung, e.g., the first anatomical entity of when the image is taken (S1608). Here, the controller 710 counts the number of pixels ($TLC_{pixels}$, $VC_{pixels}$ and $RV_{pixels}$) corresponding to each index based on density information of the taken medical image, and the number of pixels (HU) is converted into volume (ml) ($TLC_{temp}$, $VC_{temp}$ and $RV_{temp}$). Further, a predetermined index, for example, the residual volume (RV) may be determined by the counted pixels, or may be calculated using the previously determined total lung capacity (TLC) and vital capacity (VC).

The controller 710 determines at least one of the indexes (TLC, VC, RV) at the maximum inspiration or the maximum expiration, based on the indexes ($TLC_{temp}$, $VC_{temp}$, $RV_{temp}$) at the time of taking the medical image determined in the operation S1608, the volume ($L_N$) of the first anatomical entity measured in the operation S1602, and the volume ($L_M$) of the first anatomical entity at the maximum inspiration or the maximum expiration estimated in the operation S1606 (S1610).

Further, the image processing apparatus 100 provides a user (or a doctor) with the condition information about the lung, e.g., the first anatomical entity based on the indexes (TLC, VC and RV) determined in the operation S1610 (S1612). Thus, a user makes a diagnosis with regard to the first anatomical entity, e.g., the lung based on the provided condition information.

As described above, the image processing apparatus 100 according to an example embodiment determines and provides condition information of an anatomical entity at a predetermined time, for example, a lung at the maximum inspiration or expiration based on a medical image taken randomly, so that a doctor or the like user can use the condition information to make a diagnosis of the entity.

The image processing apparatus 100 according to an example embodiment makes a more accurate diagnosis since it measures and provides even RV and TLC, which are not provided by the existing vital capacity measurement (e.g., the spirometry), and is utilizable in making a diagnosis of a patent who is difficult to draw a deep breath or measure his/her vital capacity due to a pneumonectomy operation or the other reasons.

Further, the image processing apparatus 100 according to an example embodiment uses a medical image previously taken for another purpose without taking a separate medical image in order to make a diagnosis of a lung disease, and is thus utilizable in the lung CT scan requiring a relatively high examination frequency.

The features of many example embodiments may be partially or wholly coupled or combined with each other, and technically variously interworked and driven as fully understood by those skilled in the art. Further, the example embodiments may be materialized independently of each other or realized together based on a correlation.

By the way, the foregoing example embodiments may be realized in a computer-readable recording medium. The computer-readable recording medium includes a transfer medium and a storage medium for storing data readable by a computer system. The transfer medium is materialized by a wired/wireless network to which the computer system is connected.

The foregoing example embodiments may be realized by hardware and combination between hardware and software. As the hardware, the controller 710 may include a nonvolatile memory in which the software, e.g., a computer program is stored, a RAM to which the computer program stored in the nonvolatile memory is loaded, and a CPU for executing the computer program loaded to the RAM. The nonvolatile memory includes a hard disk drive, a flash memory, a ROM, CD-ROMs, magnetic tapes, a floppy disc, an optical storage, a data transfer apparatus using Internet, etc., but not limited thereto. The nonvolatile memory is a kind of computer-readable recording medium in which a program readable by a computer is recorded.

The computer program may refer, for example, to a code that is read and executed by the CPU, and includes codes for performing the operations S1602 to S1612 of the controller 710 as illustrated in FIG. 16.

The computer program may be included in an operating system provided in the image processing apparatus 100 or software including an application and/or software interfacing with an external apparatus.

Although various example embodiments have been illustrated and described, it will be appreciated by those skilled in the art that changes may be made in these example embodiments without departing from the principles and spirit of the disclosure, the scope of which is defined in the appended claims and their equivalents.

What is claimed is:

1. An image processing apparatus comprising:
a storage for storing standard information about size relationships between a plurality of anatomical entities; and
at least one processor configured:
to detect regions corresponding to the plurality of anatomical entities on a medical image obtained by scanning an object at a first point in time within a respiration cycle, the plurality of anatomical entities comprising a first anatomical entity and a second anatomical entity,
based on the standard information and the detected regions, to estimate a size of the second anatomical entity at a second point in time within the respiration cycle,
based on size relationships between the first anatomical entity and the second anatomical entity on the detected regions and the estimated size of the second anatomical entity at the second point in time, to estimate a volume of the first anatomical entity at the second point in time, and
to provide information about a condition of the first anatomical entity based on the estimated volume.

2. The image processing apparatus according to claim 1, wherein the processor is configured to determine a first estimation value corresponding to a first measurement value of the second anatomical entity based on the standard information comprising the first estimation value of third anatomical entity corresponding to the first measurement value, and to determine the volume of the first anatomical entity at the second point in time based on the first estimation value.

3. The image processing apparatus according to claim 2, the processor is configured to determine the volume of the first anatomical entity at the second point in time based on the first estimation value, the second measurement value of the first anatomical entity and the third measurement value of the third anatomical entity.

4. The image processing apparatus according to claim 3, wherein the processor is configured to determine the volume of the first anatomical entity at the second point in time based on the equation $L_M=(D_{RC} \times L_N)/D_{NC}$,
where $L_M$ is the volume of the first anatomical entity, $D_{RC}$ is the first estimation value, $L_N$ is the second measurement value, and $D_{NC}$ is the third measurement value.

5. The image processing apparatus according to claim 3, wherein the processor is configured to count a number of pixels in the medical image to determine at least one index for providing information about condition of the first anatomical entity at the first point in time for the medical image, and to determine at least one index at the second point in time based on the determined index at the first point in time and the estimated volume of the first anatomical entity at the second point in time.

6. The image processing apparatus according to claim 5, wherein the processor is configured to convert the counted number of pixels into a volume, and to determine at least one index at the second point in time based on the estimated volume of the first anatomical entity at the second point in time, the second measurement value at the first point in time for the medical image and the at least one index converted into the volume.

7. The image processing apparatus according to claim 6, wherein the index comprises at least one of: total lung capacity (TLC), vital capacity (VC) and residual volume (RV) used in a pulmonary function test.

8. The image processing apparatus according to claim 2, wherein the first anatomical entity comprises a lung, and the second point in time comprises a time of maximum inspiration or expiration, and
the processor is configured to estimate a volume of the lung at the maximum inspiration or the maximum expiration.

9. The image processing apparatus according to claim 8, wherein the second anatomical entity comprises a diaphragm, and the third anatomical entity comprises ribs, and
the first measurement value comprises a length of the diaphragm, the second measurement value comprises a volume of the lung at the first point in time for the medical image, and the third measurement value comprises a diameter of a rib cage.

10. The image processing apparatus according to claim 1, wherein the standard information is sorted based on at least one of: age, sex, height, weight and race and stored in the storage.

11. An image processing method comprising:
detecting regions corresponding to a plurality of anatomical entities on a medical image obtained by scanning an object at a first point in time within a respiration cycle, the plurality of anatomical entities comprising a first anatomical entity and a second anatomical entity;
based on a standard information about size relationships between the plurality of anatomical entities and the detected regions, estimating a size of the second anatomical entity at a second point in time within the respiration cycle;
based on size relationships between the first anatomical entity and the second anatomical entity on the detected regions and the estimated size of the second anatomical entity at the second point in time, estimating a volume of the first anatomical entity at the second point in time; and providing information about condition of the first anatomical entity based on the estimated volume.

12. The method according to claim 11, wherein the estimating the volume of the first anatomical entity comprises determining a first estimation value corresponding to a first measurement value of a second anatomical entity based on the standard information comprising the first estimation value of a third anatomical entity corresponding to the first measurement value, and determining the volume of the first anatomical entity at the second point in time from the first estimation value.

13. The method according to claim 12, wherein the estimating the volume of the first anatomical entity comprises determining the volume of the first anatomical entity at the second point in time based on the first estimation value, the second measurement value of the first anatomical entity and the third measurement value of the third anatomical entity.

14. The method according to claim 13, wherein the estimating the volume of the first anatomical entity comprises determining the volume of the first anatomical entity at the second point in time using the equation $L_M=(D_{RC} \times L_N)/D_{NC}$, where $L_M$ is the volume of the first anatomical entity, $D_{RC}$ is the first estimation value, $L_N$ is the second measurement value, and $D_{NC}$ is the third measurement value.

15. The method according to claim 13, further comprising:
counting a number of pixels in the medical image to determine at least one index for providing information about condition of the first anatomical entity at the first point in time for the medical image; and
determining at least one index at the second point in time based on the determined index at the first point in time and the estimated volume of the first anatomical entity at the second point in time,
wherein the providing information about condition of the first anatomical entity comprises providing information about the condition of the first anatomical entity based on the at least one determined index at the second point in time.

16. The method according to claim 15, further comprising converting the number of counted pixels into a volume,
wherein the determining the at least one index at the second point in time comprises determining at least one index at the second point in time based on the estimated volume of the first anatomical entity at the second point in time, the second measurement value at the first point in time for the medical image and the at least one index converted into the volume.

17. The method according to claim 16, wherein the index comprises at least one of: total lung capacity (TLC), vital capacity (VC) and residual volume (RV) used in a pulmonary function test,
the first anatomical entity comprises a lung, and the second point in time comprises time of maximum inspiration or expiration, and
the estimating the volume of the first anatomical entity comprises estimating a volume of the lung at the maximum inspiration or the maximum expiration.

18. The method according to claim 17, wherein the second anatomical entity comprises a diaphragm, and the third anatomical entity comprises ribs, and
the first measurement value comprises a length of the diaphragm, the second measurement value comprises a volume of the lung at the first point in time for the medical image, and the third measurement value comprises a diameter of a rib cage.

19. The method according to claim 11, wherein the standard information is sorted based on at least one of: age, sex, height, weight and race, and is previously stored in the storage, and the providing information about condition of the first anatomical entity comprises using a display to provide information about condition of the first anatomical entity.

20. A non-transitory computer-readable recording medium having stored thereon a program, which when executed by a processor, causes an image processing apparatus to perform operations comprising:
detecting regions corresponding to a plurality of anatomical entities on a medical image obtained by scanning an object at a first point in time within a respiration cycle, the plurality of anatomical entities comprising a first anatomical entity and a second anatomical entity;
based on a standard information about size relationships between the plurality of anatomical entities and the detected regions, estimating a size of the second anatomical entity at a second point in time within the respiration cycle;
based on size relationships between the first anatomical entity and the second anatomical entity on the detected regions and the estimated size of the second anatomical entity at the second point in time, estimating a volume of the first anatomical entity at the second point in time; and
providing information about a condition of the first anatomical entity based on the estimated volume.

* * * * *